(12) United States Patent
Byrjalsen et al.

(10) Patent No.: US 7,655,471 B2
(45) Date of Patent: Feb. 2, 2010

(54) BIOCHEMICAL MARKERS OF THE HUMAN ENDOMETRIUM

(75) Inventors: Inger Byrjalsen, Hoersholm (DK); Peter M. Larsen, Odense (DK); Stephen J. Fey, Rhus (DK)

(73) Assignee: Drugmode APS, Odense M (DK)

( * ) Notice: Subject to any disclaimer, the term of this patent is extended or adjusted under 35 U.S.C. 154(b) by 0 days.

(21) Appl. No.: 10/347,169

(22) Filed: Jan. 17, 2003

(65) Prior Publication Data

US 2006/0115812 A1    Jun. 1, 2006

Related U.S. Application Data

(63) Continuation of application No. PCT/EP01/08056, filed on Jul. 12, 2001.

(51) Int. Cl.
   *G01N 33/50* (2006.01)
   *G01N 33/53* (2006.01)

(52) U.S. Cl. .......................... 436/64; 436/501; 435/7.1; 435/7.23; 530/350; 530/387.1; 530/387.7

(58) Field of Classification Search ................... 436/64, 436/501; 435/7.1, 7.23; 530/350, 387.1, 530/387.7
   See application file for complete search history.

(56) References Cited

FOREIGN PATENT DOCUMENTS

WO    WO2005093063 A1 * 10/2005

OTHER PUBLICATIONS

Byrjalsen et al. (Mol. Hum. Reprod. Aug. 1999; 5 (8): 748-756).*
Ji et al. (Electrophoresis. Jun. 2007; 28 (12): 1997-2008).*
Lee et al. (Gynecol. Oncol. Oct. 2005; 99 (1): 142-152).*
Abdul-Rahman et al. (Electrophoresis. Jun. 2007; 28 (12): 1989-1296).*
Wataba et al. (Int. J. Cancer. Feb. 15, 2001; 91 (4): 448-456).*

* cited by examiner

*Primary Examiner*—Stephen L Rawlings
(74) *Attorney, Agent, or Firm*—Gregory B. Butler, Esq.; Edwards Angell Palmer & Dodge LLP

(57) ABSTRACT

Endometrium secreted polypeptides are assayed in body fluids to determine the presence of polypeptides of specified pI and MW values that have been found to be regulated in body fluids according to the status of the endometrium, or the presence of hyperplasia or adenocarcinoma.

2 Claims, 22 Drawing Sheets

SEQUENCE LISTING

```
<160> NUMBER OF SEQ ID NOS: 1

<210> SEQ ID NO 1
<211> LENGTH: 543
<212> TYPE: PRT
<213> ORGANISM: Homo sapiens
<300> PUBLICATION INFORMATION:
<308> DATABASE ACCESSION NUMBER: GENEMBL/P31948
<309> DATABASE ENTRY DATE: 1993-07-01
<313> RELEVANT RESIDUES IN SEQ ID NO: (1)..(543)

<400> SEQUENCE: 1
```

-continued

```
Met Glu Gln Val Asn Glu Leu Lys Glu Lys Gly Asn Lys Ala Leu Ser
1               5                   10                  15

Val Gly Asn Ile Asp Asp Ala Leu Gln Cys Tyr Ser Glu Ala Ile Lys
            20                  25                  30

Leu Asp Pro His Asn His Val Leu Tyr Ser Asn Arg Ser Ala Ala Tyr
            35                  40                  45

Ala Lys Lys Gly Asp Tyr Gln Lys Ala Tyr Glu Asp Gly Cys Lys Thr
50                  55                  60

Val Asp Leu Lys Pro Asp Trp Gly Lys Gly Tyr Ser Arg Lys Ala Ala
65                  70                  75                  80

Ala Leu Glu Phe Leu Asn Arg Phe Glu Glu Ala Lys Arg Thr Tyr Glu
                85                  90                  95

Glu Gly Leu Lys His Glu Ala Asn Asn Pro Gln Leu Lys Glu Gly Leu
            100                 105                 110

Gln Asn Met Glu Ala Arg Leu Ala Glu Arg Lys Phe Met Asn Pro Phe
            115                 120                 125

Asn Met Pro Asn Leu Tyr Gln Lys Leu Glu Ser Asp Pro Arg Thr Arg
            130                 135                 140

Thr Leu Leu Ser Asp Pro Thr Tyr Arg Glu Leu Ile Glu Gln Leu Arg
145                 150                 155                 160

Asn Lys Pro Ser Asp Leu Gly Thr Lys Leu Gln Asp Pro Arg Ile Met
                165                 170                 175

Thr Thr Leu Ser Val Leu Leu Gly Val Asp Leu Gly Ser Met Asp Glu
            180                 185                 190

Glu Glu Glu Ile Ala Thr Pro Pro Pro Pro Pro Lys Lys Glu
            195                 200                 205

Thr Lys Pro Glu Pro Met Glu Glu Asp Leu Pro Glu Asn Lys Lys Gln
    210                 215                 220

Ala Leu Lys Glu Lys Glu Leu Gly Asn Asp Ala Tyr Lys Lys Lys Asp
225                 230                 235                 240

Phe Asp Thr Ala Leu Lys His Tyr Asp Lys Ala Lys Glu Leu Asp Pro
                245                 250                 255

Thr Asn Met Thr Tyr Ile Thr Asn Gln Ala Ala Val Tyr Phe Glu Lys
            260                 265                 270

Gly Asp Tyr Asn Lys Cys Arg Glu Leu Cys Glu Lys Ala Ile Glu Val
            275                 280                 285

Gly Arg Glu Asn Arg Glu Asp Tyr Arg Gln Ile Ala Lys Ala Tyr Ala
        290                 295                 300

Arg Ile Gly Asn Ser Tyr Phe Lys Glu Glu Lys Tyr Lys Asp Ala Ile
305                 310                 315                 320

His Phe Tyr Asn Lys Ser Leu Ala Glu His Arg Thr Pro Asp Val Leu
                325                 330                 335

Lys Lys Cys Gln Gln Ala Glu Lys Ile Leu Lys Glu Gln Glu Arg Leu
            340                 345                 350

Ala Tyr Ile Asn Pro Asp Leu Ala Leu Glu Glu Lys Asn Lys Gly Asn
            355                 360                 365

Glu Cys Phe Gln Lys Gly Asp Tyr Pro Gln Ala Met Lys His Tyr Thr
            370                 375                 380

Glu Ala Ile Lys Arg Asn Pro Lys Asp Ala Lys Leu Tyr Ser Asn Arg
385                 390                 395                 400

Ala Ala Cys Tyr Thr Lys Leu Leu Glu Phe Gln Leu Ala Leu Lys Asp
                405                 410                 415

Cys Glu Glu Cys Ile Gln Leu Glu Pro Thr Phe Ile Lys Gly Tyr Thr
```

-continued

```
              420                 425                 430
Arg Lys Ala Ala Ala Leu Glu Ala Met Lys Asp Tyr Thr Lys Ala Met
            435                 440                 445
Asp Val Tyr Gln Lys Ala Leu Asp Leu Asp Ser Ser Cys Lys Glu Ala
        450                 455                 460
Ala Asp Gly Tyr Gln Arg Cys Met Met Ala Gln Tyr Asn Arg His Asp
465                 470                 475                 480
Ser Pro Glu Asp Val Lys Arg Arg Ala Met Ala Asp Pro Glu Val Gln
                485                 490                 495
Gln Ile Met Ser Asp Pro Ala Met Arg Leu Ile Leu Glu Gln Met Gln
            500                 505                 510
Lys Asp Pro Gln Ala Leu Ser Glu His Leu Lys Asn Pro Val Ile Ala
        515                 520                 525
Gln Lys Ile Gln Lys Leu Met Asp Val Gly Leu Ile Ala Ile Arg
        530                 535                 540
```

BIOCHEMICAL MARKERS OF THE HUMAN ENDOMETRIUM

Figure 1:
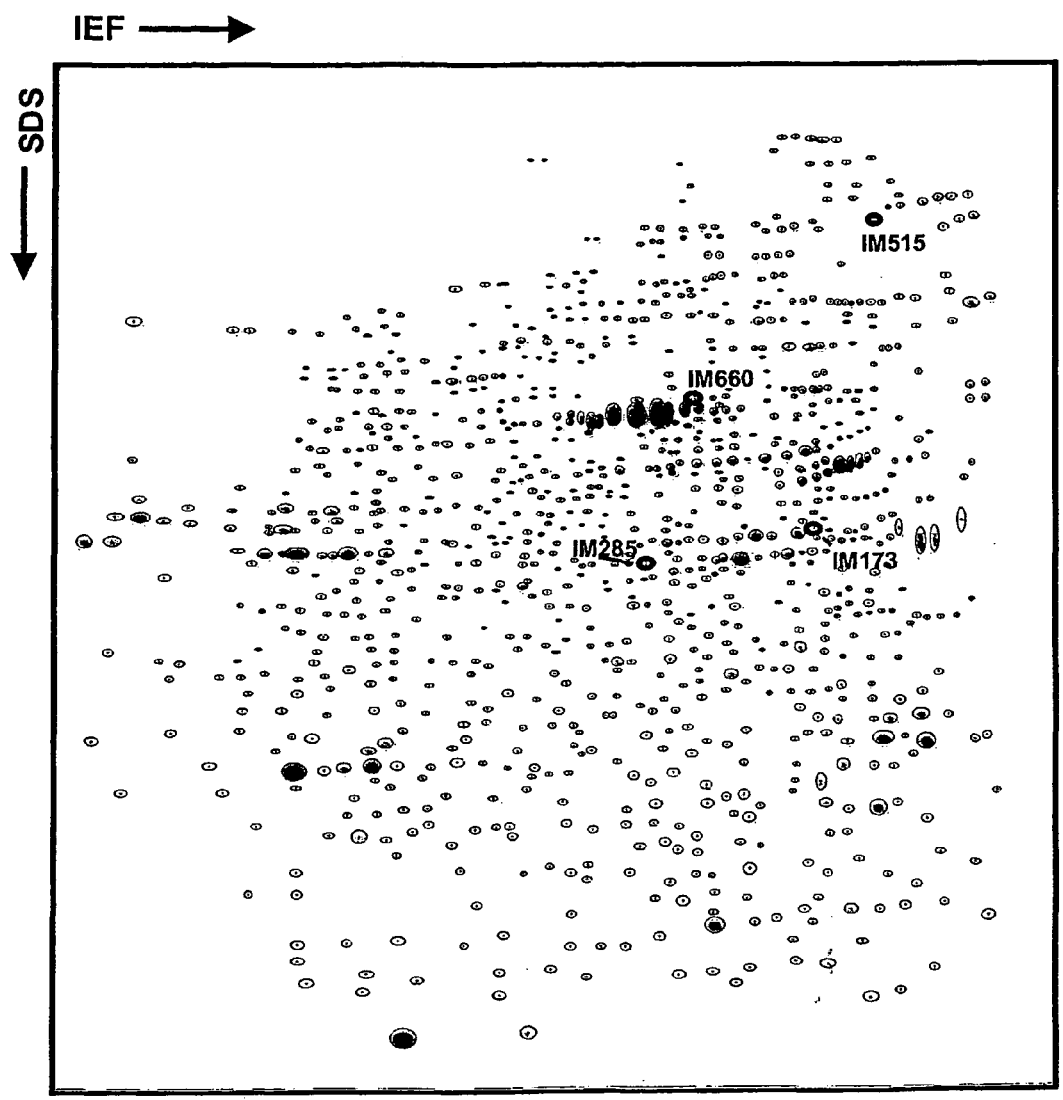

The present application is a continuation of PCT International Application Number PCT/EP01/08056 as filed on 12 Jul. 2001, which application claims priority to GB 001 7716.2 as filed on 19 Jul. 2000.

The endometrium is the mucous lining of the uterine cavity. During the menstrual cycle, the endometrium is the organ in the body that shows the greatest changes under the influence of the sex hormones, oestradiol and progesterone. In the oestrogen dominated phase the endometrium proliferates until progesterone from the corpus luteum transforms the oestrogen-primed proliferative endometrium to a secretory phase endometrium. In due course this is followed by shedding of the fully transformed endometrium during the menstruation, and a new cycle will begin.

Persistent unbalanced oestrogen stimulation either due to increased endogenous production of oestrogens, or replacement therapy in which oestrogens are given alone, is associated with increased risk of developing endometrial hyperplasia and subsequently endometrial adenocarcinoma. Histologically, these pathological conditions are characterised by increased thickness of the endometrium and irregular pattern of the endometrial glandular cells.

Edometrial adenocarcinoma is a life threatening condition.

As indicated above, under influence of the sex hormones, oestradiol and progesterone, the human endometrium undergoes cyclical variation with an oestrogen-dominated phase, i.e. the proliferative phase, an ovulation phase, i.e. the interval phase, a progesterone-dominated phase, i.e. the secretory phase, and finally the endometrium is shed, i.e. the menstrual phase. The same cyclical variation of the endometrium is seen in postmenopausal women receiving sequentially combined hormone replacement therapy. The demand for endometrial status assessment has increased greatly in the last decade, not only on account of the extensive research into fertility, but also in order to estimate endometrial response to the large number of combined oestrogens/progestogen preparations used in hormone replacement therapy. At present the endometrial status is assessed by histological and biochemical analysis of endometrial biopsies. This is time-consuming, expensive and causes discomfort for the woman. It would be highly desirable to identify biochemical markers which could be measured in body fluids reflecting the endometrial status, obviating the need for endometrial biopsies. The detection of such markers in histological samples would also however be advantageous as an additional method of recognising the histological status of such samples. Studies have suggested that serum placental protein 14 (PP14), which is produced in the glandular cells of the secretory phase endometrium (Ref. 3), is a reliable marker of the secretory phase endometrium. It has been shown that serum PP14 strongly correlates with the secretory activity of the endometrium in postmenopausal women receiving hormone replacement therapy (Ref. 4,5). No similar marker exists for the proliferative phase endometrium and other markers for the secretory phase would be desirable.

WO98/10291, Ref. 1 and Ref. 2 describe the use of 2D gel electrophoresis to identify proteins in endometrial tissue homogenates which are present in increased amounts in hyperplasia, or in adenocarcinoma or in proliferative phase endometrium as against secretory phase endometrium. However, secreted proteins were washed away, so the proteins identified were not necessarily secreted by the endometrium in increased amounts but rather are expected to have been proteins retained within or bound on the surface of the cells of the endometrium. For use as targets in assays conducted on body fluids it would be desirable to identify proteins that are secreted in different amounts according to the tissue status. We have now discovered that certain proteins are produced and secreted by the endometrium in increased amounts associated with hyperplasia and/or adenocarcinoma, or the secretory or proliferative phase of the endometrium and that certain proteins are produced and secreted in decreased amounts in hyperplasia and/or adenocarcinoma or in the secretory or proliferative phase of the endometrium. The present invention relates in a first aspect to assay methods based on said proteins.

Unless otherwise indicated, references to the proteins herein include references to modified forms of the proteins and derivatives of the proteins, including but not restricted to glycosylated, phosphorylated, acetylated, methylated or lipidated forms thereof.

Thus the invention provides a method of characterising a sample of body fluid from a mammal comprising detecting or quantitating therein one or more polypeptides or detecting or quantitating a fragment or breakdown product thereof, or a nucleic acid coding therefor or antibodies thereto, which polypeptides are each secreted by the endometrium in an amount which differs according to whether the endometrium is characterised by at least one of the following conditions:

a) being in the proliferative phase b) being in the secretory phase c) hyperplasia or d) adenocarcinoma which increased or decreased secretion is demonstrable by 2D gel electrophoresis comparison of conditioned media of endometrial biopsy explants of endometrium showing proliferative phase histology or of endometrium showing secretory phase histology, or of endometrium showing hyperplasia, or of endometrium showing adenocarcinoma with conditioned media of endometrial biopsy explants showing a different one of proliferative phase histology, secretory phase histology, hyperplasia or adenocarcinoma, and in the case of a polypeptide secreted by the endometrium in an amount which differs according to whether the endometrium is characterised by being in the proliferative phase, correlating the presence or amount of said polypeptide or fragment or breakdown product thereof, or a nucleic acid coding therefor or antibodies thereto with the likelihood of the endometrium being in the proliferative phase, or in the case of a polypeptide secreted by the endometrium in an amount which differs according to whether the endometrium is characterised by being in the secretory phase, correlating the presence or amount of said polypeptide or fragment or breakdown product thereof, or a nucleic acid coding therefor or antibodies thereto with the likelihood of the endometrium being in the secretory phase, or in the case of a polypeptide secreted by the endometrium in an amount which differs according to whether the endometrium is characterised by hyperplasia, correlating the presence or amount of said polypeptide or fragment or breakdown product thereof, or a nucleic acid coding therefor or antibodies thereto with the likelihood of the endometrium being characterised by hyperplasia, or in the case of a polypeptide secreted by the endometrium in an amount which differs according to whether the endometrium is characterised by adenocarcinoma, correlating the presence or amount of said polypeptide or fragment or breakdown product thereof, or a nucleic acid coding therefor or antibodies thereto with the likelihood of the endometrium being characterised by adenocarcinoma, each said polypeptide being characterised by one of the following combinations of molecular weight and pI values:

| MW ± 10% (kDa) | pI ± 0.25 |
| --- | --- |
| Increased in hyperplasia | |
| 44.2 | 5.5 |
| 124.1 | 4.6 |
| 66.2 | 5.3 |
| 20.8 | 7.9 |
| Decreased in hyperplasia | |
| 24.4 | 5.3 |
| Increased in adenocarcinoma | |
| 55.7 | 5.8 |
| 82.1 | 4.9 |
| 50.4 | 5.9 |
| 43.8 | 5.1 |
| 26.6 | 6.5 |
| 62.6 | 7.4 |
| 43.1 | 8.6 |
| 53.6 | 8.3 |
| Decreased in adenocarcinoma | |
| 30.5 | 4.7 |
| 46.6 | 4.7 |
| 57.6 | 6.9 |
| 52.1 | 6.6 |
| 42.0 | 5.3 |
| 46.8 | 4.8 |
| 34.8 | 6.1 |
| 50.0 | 6.4 |
| 28.0 | 5.2 |
| 86.2 | 4.6 |
| 55.5 | 5.6 |
| 47.2 | 5.0 |
| 46.5 | 4.8 |
| 34.5 | 6.3 |
| 55.5 | 5.5 |
| 56.2 | 5.4 |
| 56.0 | 5.3 |
| 22.0 | 5.2 |
| 20.0 | 4.8 |
| 15.4 | 5.3 |
| 139.4 | 5.0 |
| 57.8 | 5.3 |
| 55.5 | 6.6 |
| 50.0 | 6.4 |
| 53.3 | 6.3 |
| 46.3 | 4.4 |
| 32.7 | 6.3 |
| 28.3 | 4.8 |
| 23.8 | 6.3 |
| 130.7 | 7.7 |
| 55.3 | 7.3 |
| 58.2 | 7.3 |
| 35.1 | 7.9 |
| 39.8 | 7.2 |
| 38.4 | 7.2 |
| 36.9 | 7.6 |
| 111.0 | 7.8 |
| 36.0 | 7.9 |
| 37.3 | 7.5 |
| Increased in hyperplasia and adenocarcinoma | |
| 61.6 | 5.8 |
| 92.5 | 5.5 |
| 60.0 | 5.8 |
| 62.8 | 6.4 |
| 63.5 | 5.4 |
| 63.2 | 5.5 |
| 60.6 | 5.2 |
| 59.7 | 6.2 |
| 59.9 | 5.9 |
| 62.5 | 5.7 |
| 65.5 | 7.9 |
| 53.5 | 8.4 |
| 23.1 | 8.4 |
| 55.9 | 8.5 |
| 55.4 | 8.4 |

-continued

| MW ± 10% (kDa) | pI ± 0.25 |
| --- | --- |
| Decreased in hyperplasia and adenocarcinoma | |
| 20.1 | 5.2 |
| 27.4 | 4.9 |
| 67.7 | 4.8 |
| 28.6 | 4.9 |
| 42.4 | 6.0 |
| 58.5 | 5.0 |
| 24.1 | 4.9 |
| 51.4 | 6.5 |
| 46.2 | 6.3 |
| 45.0 | 5.8 |
| 39.6 | 6.4 |
| 23.2 | 5.3 |
| 60.4 | 7.1 |
| Increased in proliferative phase | |
| 57.8 | 5.2 |
| 56.2 | 5.2 |
| 58.3 | 4.9 |
| 36.1 | 5.3 |
| 86.3 | 4.6 |
| 33.9 | 4.9 |
| 34.4 | 4.9 |
| 32.6 | 5.0 |
| 57.5 | 5.1 |
| 41.9 | 5.4 |
| 60.6 | 5.0 |
| 86.4 | 4.5 |
| 55.7 | 5.4 |
| 60.8 | 5.0 |
| 46.6 | 4.4 |
| 32.5 | 5.2 |
| 55.8 | 5.2 |
| 31.9 | 5.8 |
| 118.6 | 7.5 |
| 120.0 | 7.4 |
| Increased in hyperplasia and proliferative phase | |
| 36.3 | 4.4 |
| 58.5 | 5.2 |
| 52.1 | 6.0 |
| 32.6 | 6.8 |
| 46.8 | 4.7 |
| 27.5 | 6.4 |
| 32.8 | 5.1 |
| 34.2 | 7.6 |
| Decreased in proliferative phase | |
| 76.1 | 5.8 |
| Increased in secretory phase | |
| 28.2 | 4.7 |
| 28.9 | 4.6 |
| 70.5 | 4.9 |
| 75.1 | 4.7 |
| 18.0 | 6.0 |
| 145.4 | 5.5 |
| 144.1 | 5.4 |
| 142.9 | 5.3 |
| 143.9 | 5.2 |
| 44.6 | 5.9 |
| 23.6 | 5.2 |
| 25.2 | 4.8 |
| 34.2 | 8.5 |
| 130.6 | 7.9 |
| 38.2 | 9.3 |
| 27.9 | 7.8 |
| Decreased in secretory phase | |
| 53.4 | 5.7 |
| 26.3 | 6.5 |

The proteins or polypeptides which are demonstrated to be secreted in altered amounts by the 2D gel electrophoresis procedure described herein may be complete proteins or may be fragments of proteins found in the body in other contexts. Where the polypeptides are or appear to be fragments of identifiable complete proteins, this may be because the complete protein is expressed in endometrial cells initially and is subject to fragmentation at some time before or after secretion. It may be because the fragments are exposed in that form either normally or when the endometrium is characterised by one or more of the described conditions.

Where such fragments are to be found by the 2D gel electrophoresis procedure described, the method of sample characterisation of the invention may be directed to detect or quantitate such fragments and/or the corresponding complete proteins or to the detection of fragments of the disclosed fragments or different fragments of the complete protein.

Preferred methods according to the invention include forming a mathematical comparison of the amount of a first polypeptide, a breakdown product thereof, a nucleic acid coding for said first polypeptide or an antibody to said first polypeptide and the amount of a second polypeptide, a breakdown product thereof, a nucleic acid coding for said second polypeptide or an antibody to said second polypeptide, wherein said first polypeptide is secreted in increased or decreased amounts in hyperplasia or in adenocarcinoma as compared to normal endometrium, and said second polypeptide is secreted in increased or decreased amounts in hyperplasia or adenocarcinoma as compared to normal endometrium.

A protein or polypeptide may be a useful marker of either hyperplasia or adenocarcinoma if its level of expression in either of these conditions is significantly higher than its level of expression in normal endometrium. If the expression level varies in normal endometrium according to whether it is the proliferative or secretory phase, the protein or polypeptide may be a useful marker if its level of expression is significantly greater than the higher of the proliferative and secretory phase levels.

Similarly, a protein or polypeptide may be a useful marker of either hyperplasia or adenocarcinoma if its expression level in one or both of these conditions is significantly lower than in whichever of proliferative or secretory phase endometrium provides the lower level of expression.

Alternatively, one may form a mathematical comparison of the amount of a first polypeptide, a breakdown product thereof, a nucleic acid coding for said first polypeptide or an antibody to said first polypeptide and the amount of a second polypeptide, a breakdown product thereof, a nucleic acid coding for said second polypeptide or an antibody to said second polypeptide, wherein said first polypeptide is secreted in increased or decreased amounts in secretory phase endometrium as compared to proliferative phase endometrium, and said second polypeptide is secreted in increased or decreased amounts in secretory phase endometrium as compared to proliferative phase endometrium.

Alternatively, one may form a mathematical comparison of the amount of a first polypeptide, a breakdown product thereof, a nucleic acid coding for said first polypeptide or an antibody to said first polypeptide and the amount of a second polypeptide, a breakdown product thereof, a nucleic acid coding for said second polypeptide or an antibody to said second polypeptide, wherein said first polypeptide is secreted in increased or decreased amounts in proliferative phase endometrium as compared to secretory phase endometrium, and said second polypeptide is secreted in increased or decreased amounts in proliferative phase endometrium as compared to secretory phase endometrium.

Preferably, said mathematical comparison is a sum, difference, product or ratio.

For instance one may take the sum or product of two or more increased markers or the difference or ratio of an increased and a decreased marker.

The proteins or polypeptide being regulated in hyperplasia and/or adenocarcinoma are up- or down-regulated as compared to their expression in normal endometrium proliferative and secretory phase.

It will be appreciated that the assay itself need not be conducted by a method involving 2D gel electrophoresis. The proteins or polypeptides that are the subject of the assay procedures of the invention are identifiable and definable by the stated 2D gel electrophoresis but it is not envisaged that this will be the most convenient method for routine assay use.

The polypeptides upon which an assay method of the invention is based may be such that when subjected to mass spectrometry fingerprinting by trypsin fragmentation followed by MALDI-TOF mass spectrometry of the resulting fragments produce a mass spectrometry fingerprint consistent with being one of the following proteins or with being fragments thereof:

TABLE 1

| Identifier | Protein name |
|---|---|
| Endometrial proteins with increased synthesis in hyperplasia | |
| sp|P07476 | Involucrin |
| sp|P38646 | Mortalin-2 |
| Endometrial proteins with increased synthesis in adenocarcinoma | |
| sp|P17987 | T-complex polypeptide 1 |
| sp|P07900 | Heat shock protein HSP-90 beta |
| sp|Q08945 | Structure specific recognition protein 1 fragment including at least residues: 37-413 |
| sp|P04270 | α, β, or γ-actin |
| sp|P02570 | |
| sp|P02571 | |
| pir|I59377 | Template activating factor-1, alpha |
| sp|P17936 | Insulin-like growth factor binding protein 3 |
| sp|Q92841 | DEAD/H box polypeptide 17 fragment including at least residues: 30-449 |
| Endometrial proteins with decreased synthesis in adenocarcinoma | |
| sp|P02570 | β or γ-actin fragment including at least residues: |
| sp|P02571 | 29-206 |
| sp|P00367 | Glutamate dehydrogenase |
| sp|Q9UJZ1 | Stomatin like protein 2 |
| sp|P04350 | Tubulin beta 5 |
| sp|P04083 | Annexin I |
| gi|5803113 | Transmembrane protein ER |
| sp|p07711 | Cathepsin L |
| sp|P04083 | Annexin 1 |
| sp|O43390 | Heterogeneous nuclear ribonucleoprotein R |
| sp|P50990 | Chaperonin containing TCP1 subunit 8 |
| sp|P50990 | Chaperonin containing TCP1 subunit 8 |
| sp|Q9Y4L1 | Oxygen related protein |
| sp|P04083 | Annexin 1 |
| sp|O75334 | Liprin-alpha 2 |
| sp|P00367 | Glutamate dehydrogenase |
| sp|P00367 | Glutamate dehydrogenase |
| sp|P00338 | L-Lactate dehydrogenase M chain |
| sp|P07355 | Annexin II |
| sp|P40925 | Malate dehydrogenase, cytoplasmic |
| Endometrial proteins with increased synthesis in hyperplasia and adenocarcinoma | |
| sp|O43707 | Actinin, alpha 4 |
| sp|P31948 | Stress induced phosphoprotein 1 |
| sp|P311948 + sp|P31939 | Stress induced phoshoprotein 1 + purH |
| sp|P31948 | Stress induced phosphoprotein 1 (SEQ ID NO: 1) |
| sp|P31948 | Stress induced phosphoprotein 1 |
| sp|P52272 | Heterogeneous nuclear ribonucleoprotein M |

TABLE 1-continued

| Identifier | Protein name |
| --- | --- |
| sp|Q92841 | DEAD/H box polypeptide 17 fragment including at least residues: 30-449 |
| sp|Q06830 | Peroxiredoxin 1 |
| *Endometrial proteins with decreased synthesis in hyperplasia and adenocarcinoma* | |
| sp|P08729 | Keratin 7 fragment including at least residues: 52-225 |
| sp|P02570 sp|P02571 | β or γ-actin fragment including at least residues: 29-206 |
| sp|Q9NY65 | Tubulin, alpha 8 |
| gi|13630152 | Hypothetical protein FLJ10849 |
| sp|Q9GZM7 | P3ECSL |
| *Endometrial proteins with increased synthesis in proliferative phase endometrium* | |
| sp|P10809 | 60 kDA Heat shock protein |
| gi|3420929 | Tubulin, alpha isoform 1 |
| sp|P30464 | HLA class I histocompatibility antigen, alpha chain |
| sp|Q9BW10 | Tubulin, beta 4 |
| sp|P49903 | Selenophosphate synthetase |
| sp|P50990 | T-complex protein 1, theta subunit |
| gi|12737610 | Keratin 7 |
| gi|1314645 | Cytoplasmic dynein heavy chain 2 fragment including at least residues 146-273 |
| *Endometrial proteins with increased synthesis in hyperplasia and proliferative phase endometrium* | |
| sp|O43707 | Actinin, alpha 4 fragment including at least residues: 301-771 |
| sp|P10768 | Esterase D |
| sp|P19623 | Spermidine synthase |
| *Endometrial proteins with increased, synthesis in secretory phase endometrium* | |
| sp|P42655 | 14-3-3 Protein epsilon |
| sp|P12324 | Tropomyosin, cytoskeletal type |
| sp|Q09666 | Neuroblast associated differentiation associated protein AHNAK fragment including at least residues: 612-1419 |
| sp|Q09666 | Neuroblast associated differentiation associated protein AHNAK fragment including at least residues: 612-1419 |
| sp|Q09666 | Neuroblast associated differentiation associated protein AHNAK fragment including at least residues: 612-1419 |
| sp|Q09666 | Neuroblast associated differentiation associated protein AHNAK fragment including at least residues: 612-1419 |
| sp|P21796 | Voltage-dependent anion channel 1 |
| sp|O75334 | Liprin-alpha 2 |
| *Endometrial proteins with decreased synthesis in secretory phase endometrium* | |
| sp|P30101 | Protein disulfide isomerase ER60 |

Said polypeptide on which the assay is based may be a protein listed above or any characteristic fragment thereof, i.e. one of sufficient length to identify the fragment as being derived from the protein.

Figure 22:
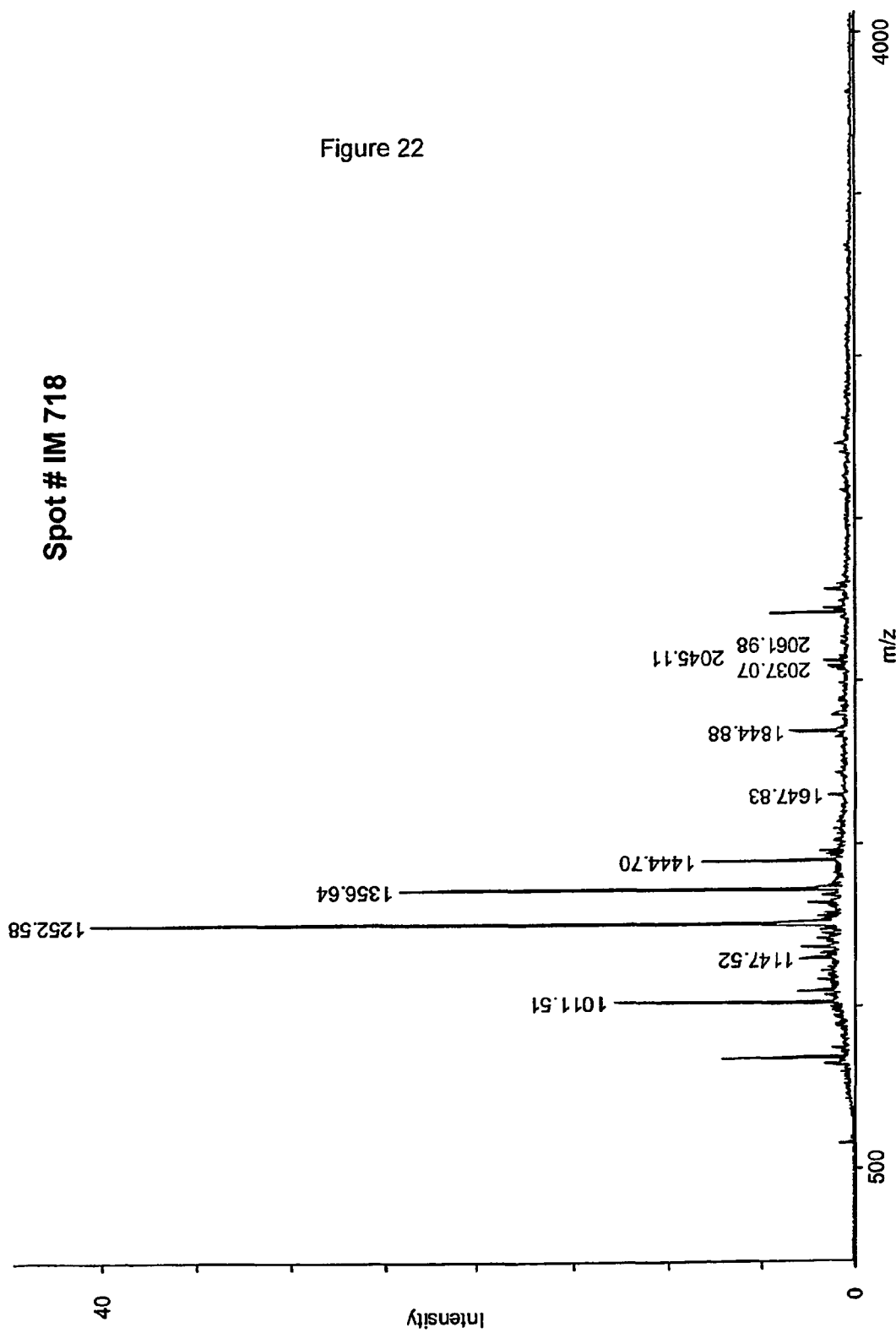

The proteins present in the conditioned medium from the culture of endometrial biopsy enplants may be separated into individual spots by the known process of 2D gel electrophoresis. The protein or proteins present in individual spots may be identified in a known manner by excision from the gel followed by fragmentation using trypsin to cut the proteins at arginine or lysine residues and the use of MALDI-TOF mass spectrometry to fingerprint the protein by the molecular weights of the range of fragments produced (spectrometric peptide mapping). An example of the mass spectrometry fingerprint obtained this way is seen in FIG. 22. This has been done for several of the proteins identified as being of interest for measurement according to the present invention. Tables 1 to 11 below list the proteins to be detected or quantitated according to the invention together with the name of the known protein which matches the mass spectrometry fingerprint of the trypsinated protein as found. The predicted molecular weight of the intact named protein is given also. In some cases it appears that the protein found is the entire named protein. In other cases, the protein found appears to be a fragment of the named protein. Identification of the detected proteins in this way depends on a corresponding protein having been discovered previously, it having been subjected to mass-spectrometry fingerprinting, and the results having been included in a searchable data-base. In some cases, we have not so far matched the protein in a spot from the 2D gel electrophoresis to a know protein (e.g. spot ID IM997 etc.).

Some of the proteins which have been identified by spectrometric peptide mapping will be discussed in more detail.

Spots NM120 and NM158 both derive from the protein DEAD/H box polypeptide 17 (p72). This is an RNA helicase, which is a nuclear protein believed to be down regulated during differentiation. It has no previously known role in adenocarcinoma. We have not found it to be expressed differently in lysates of adenocarcinoma tissue compared to normal endometrium.

Spots IM470, IM682, IM530 and IM679 relate to Hop (stress induced phosphoprotein 1, Hsp70/Hsp90-organising protein). This participates in steriod receptor assembly. We have not found it to be up or down regulated in adenocarcinoma tissue.

Spot IM939 relates to actin, a highly conserved protein involved in cell motility and in maintenance of the cytoskeleton. We do not find it to be either up or down regulated in adenocarcinoma tissue.

Spot IM924 relates to protein SSRP1 (structure specific recognition protein-1), a nuclear protein that binds to DAN structural elements.

Spot IM993 relates to template activating factor-1, alpha form, or TAF-1α, which stimulates replication and transcription by binding histones. The fragment found is an N-terminal fragment truncated in the C-terminal acidic region. It has not been found in adenocarinoma cell lysate.

Spot IM459 relates to actinin alpha (actinin 4), which cross-links actin filaments. Cellular compartment localisation of α-actinin-4 has been studied previously in connection with breast cancer. Cytoplasmic localisation (as compared to nuclear localisation) was associated with a poorer prognosis. Cytoplasmic α-actinin-4 is suggested to regulate the actin cytoskeleton and to be associated with cell motility and metastatic potential (Honda K. et al).

Spot NM99 relates to insulin like growth factor binding protein 3, a glycosylated protein that binds to IGF and regulates its activity.

Said polypeptide, fragment, breakdown product, antibody or nucleic acid is to be detected in a body fluid sample. Suitable body fluid samples include serum, blood, plasma, spectrum, urine or tear fluid.

The invention includes an immunological binding partner specifically reactive with a polypeptide as defined above, with a fragment or breakdown product thereof, or with a nucleic acid coding therefor. Immunological binding partners include both antibodies and antibody fragments retaining specific binding affinity.

The invention also includes a cell line producing a monoclonal antibody being such an immunological binding partner.

The invention includes also an assay kit for use in such an analysis method comprising an immunological binding partner as described.

Assay methods according to the invention may be for detecting the phase of the endometrium, or for detecting oestrogen-stimulation of the endometrium. Alternatively, they may be for detecting hyperplasia or adenocarcinoma.

This aspect of the invention includes a method of determining the proliferative/secretory phase status of the endometrium, and a method for determining oestrogen stimulation of the endometrium comprising the quantitative or qualitative measurement in a sample of any one or more of the polypeptides defined above or a breakdown product or fragment thereof. It also includes an immunological binding partner for any of the said polypeptides, breakdown products or fragments or a cell line producing such a binding partner.

Whilst the sequences and properties of polypeptides discussed above relate to human proteins, the assay procedures of the invention may be practised on samples arising from other species. Especially in this context, references to proteins or polypeptides herein should be understood to include proteins or having a degree of homology of at least 60% with the amino acid sequences of the given proteins or polypeptides irrespective of any modifications of said amino acids. When determining homology, modified amino acids such as phosphorylated, acetylated, amidated, methylated, glycosylated or lipidated derivatives of an amino acid should thus be considered to be the same as the amino acid without any such modification. Such polypeptides may be derived from similar proteins from other species, e.g. other mammals such as mouse, rabbit, guinea pig, pig, or cow or may be entirely or predominantly of synthetic origin.

The degree of homology may be advantageously be at least 65%, or at least 70%. Under certain circumstances, it is advantageous that the degree of homology is even higher such as at least 80% or at least 90%. Other DNA sequences which encode substantially the same amino acid sequence as a gene encoding a marker protein, i.e. a marker gene, may be used in the practice of the present invention. These include, but are not limited to, allelic genes and homologous genes from other species.

Nucleic acid fragments comprising a nucleotide sequence which codes for a protein described above or a peptide derived from it as well as nucleic acid fragments which hybridise with these nucleic acid fragments or a part thereof under stringent hybridisation conditions, e.g. 5 mM monovalent ions (0.1×SSC), neutral pH and 65° C. are important aspects of the invention. The term "highly stringent", when used in conjunction with hybridisation conditions, is as defined in the art, i.e. 5-10° C. under the melting point $T_m$, cf, Sambrook et al, 1989, pages 11.45-11.49.

By the term "nucleic acid" is meant a polynucleotide of high molecular weight which can occur as either DNA or RNA and may be either single-stranded or double-stranded.

Once the amino acid sequences of the proteins or polypeptides of utility in the present invention are known, it is possible to synthesise DNA or RNA probes which may be used for:
  i) direct detection of DNA and RNA expressing said proteins on a fixed or frozen tissue section using, e.g. chromogenous, chemiluminescent or immuno-fluorescent techniques;
  ii) polymerase chain reaction (PCR) or other amplification techniques; and
  iii) locating the part or all of the gene, isogene, pseudogene or other related genes either in cDNA libraries, genomic libraries or other collections of genetic material from either the host or other animals, including man.

In another aspect, the invention relates to a binding means which specifically binds to a relevant protein or peptide or nucleic acid fragment as described above. In particular, the invention relates to an antibody which specifically binds to a relevant protein or peptide or an antigen-binding fragment thereof, i.e. a polyclonal antibody, a monoclonal antibody, chimeric antibody, single chain antibody fragment, Fab and Fab' fragments, and an Fab expression library.

It is contemplated that both monoclonal and polyclonal antibodies will be useful in providing the basis for one or more assays to detect relevant peptides and proteins. Antibodies which are directed against epitopes that are specific for the proteins will be most useful as cross reaction will be minimised therewith.

Based upon the identification of relevant proteins described above, assay methods and kits may be produced according to standard methodology. Thus, the proteins may be obtained in purified form, either by extraction from tissues or cell lines, or by synthesis, and antibodies may be raised thereto or to characterising peptide sequences thereof.

Standard assay formats employing such antibodies may be utilised according to the invention.

Preferred immunoassays are contemplated as including various types of enzyme linked immunoassays (ELISA), immunoblot techniques, and the like, known in the art. However, it is readily appreciated that utility is not limited to such assays, and useful embodiments including RIAs and other non-enzyme linked antibody binding assays or procedures. The proteins themselves or peptides derived from the protein sequences may be used in detecting auto-antibodies to such proteins.

The invention will be illustrated and explained further by the following description in which the Figures as follows:

FIG. 1: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with increased synthesis in hyperplasia are indicated.

Figure 2:
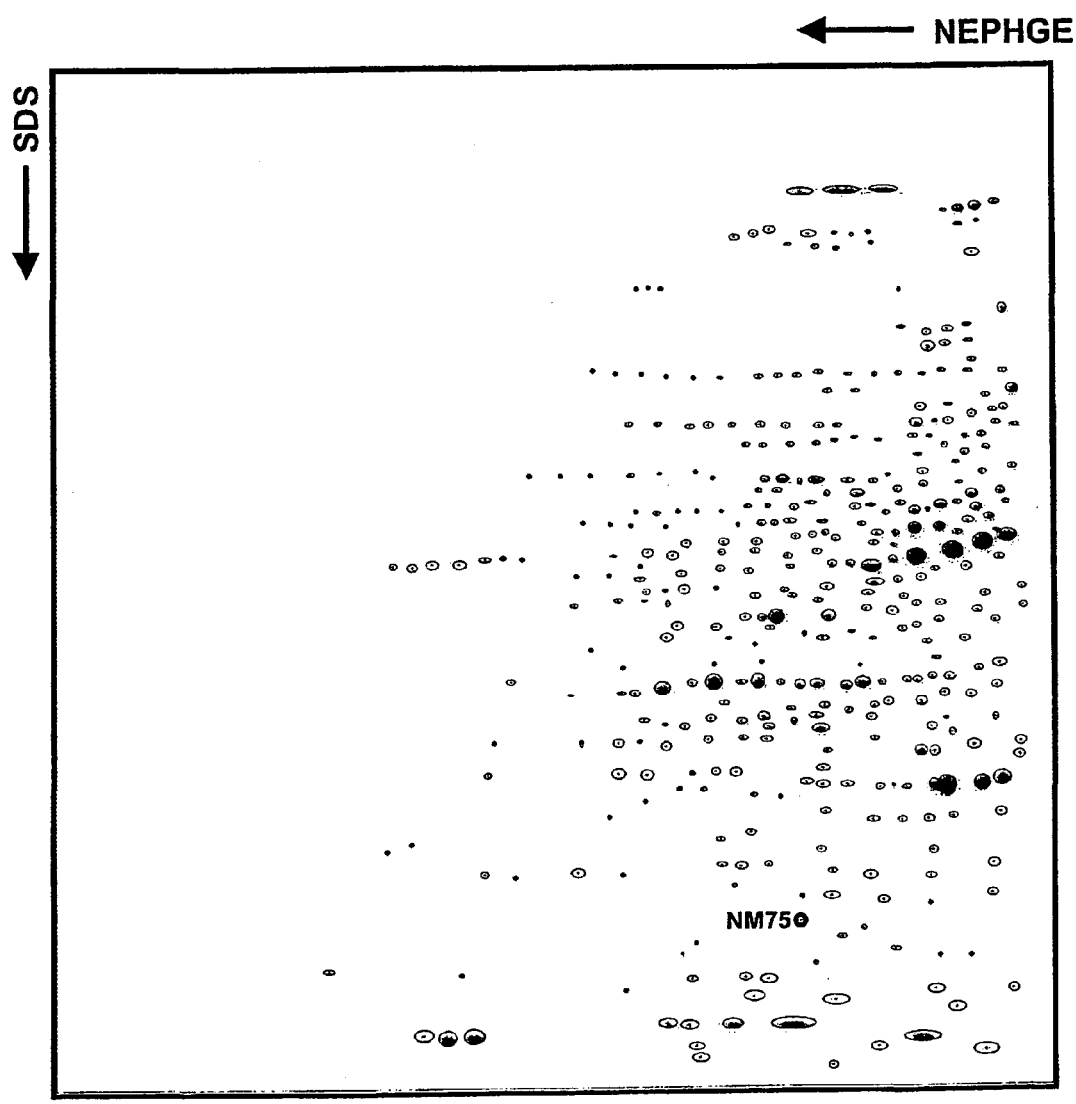

FIG. 2: Phosphoimage composite of two-dimensional gel electrophoresis of [$^{35}$S]methionine labelled endometrial proteins in conditioned medium separated in the first dimension by non-equilibrium pH gradient gel electrophoresis (NEPHGE; pI 6.5-11) and in the second dimension by sodium dodecyl sulphate polyacrylamide gel electrophoresis. The location of the spot with increased synthesis in hyperplasia is indicated.

Figure 3:
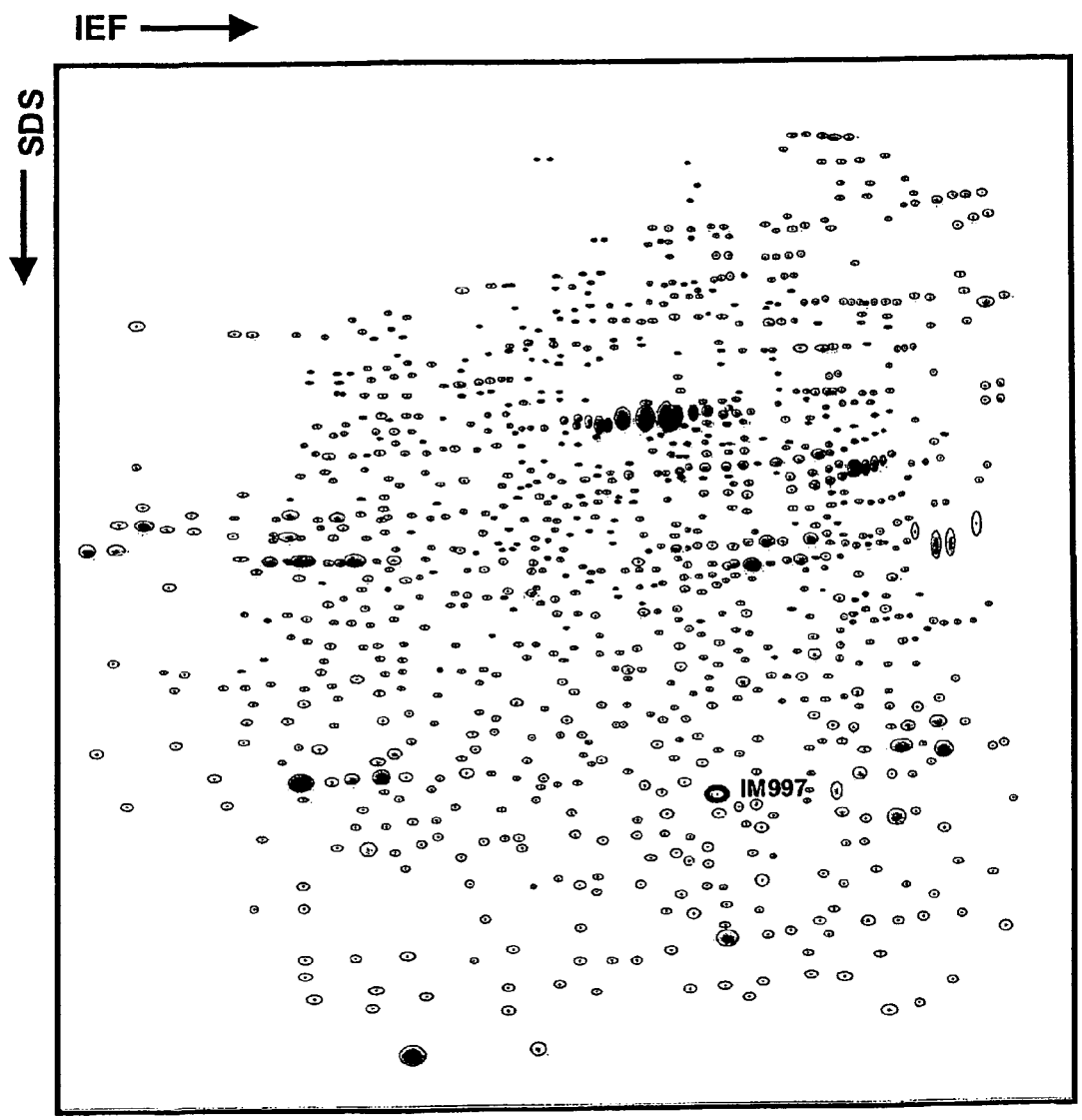

FIG. 3: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The location of the spot with decreased synthesis in hyperplasia is indicated.

Figure 4:
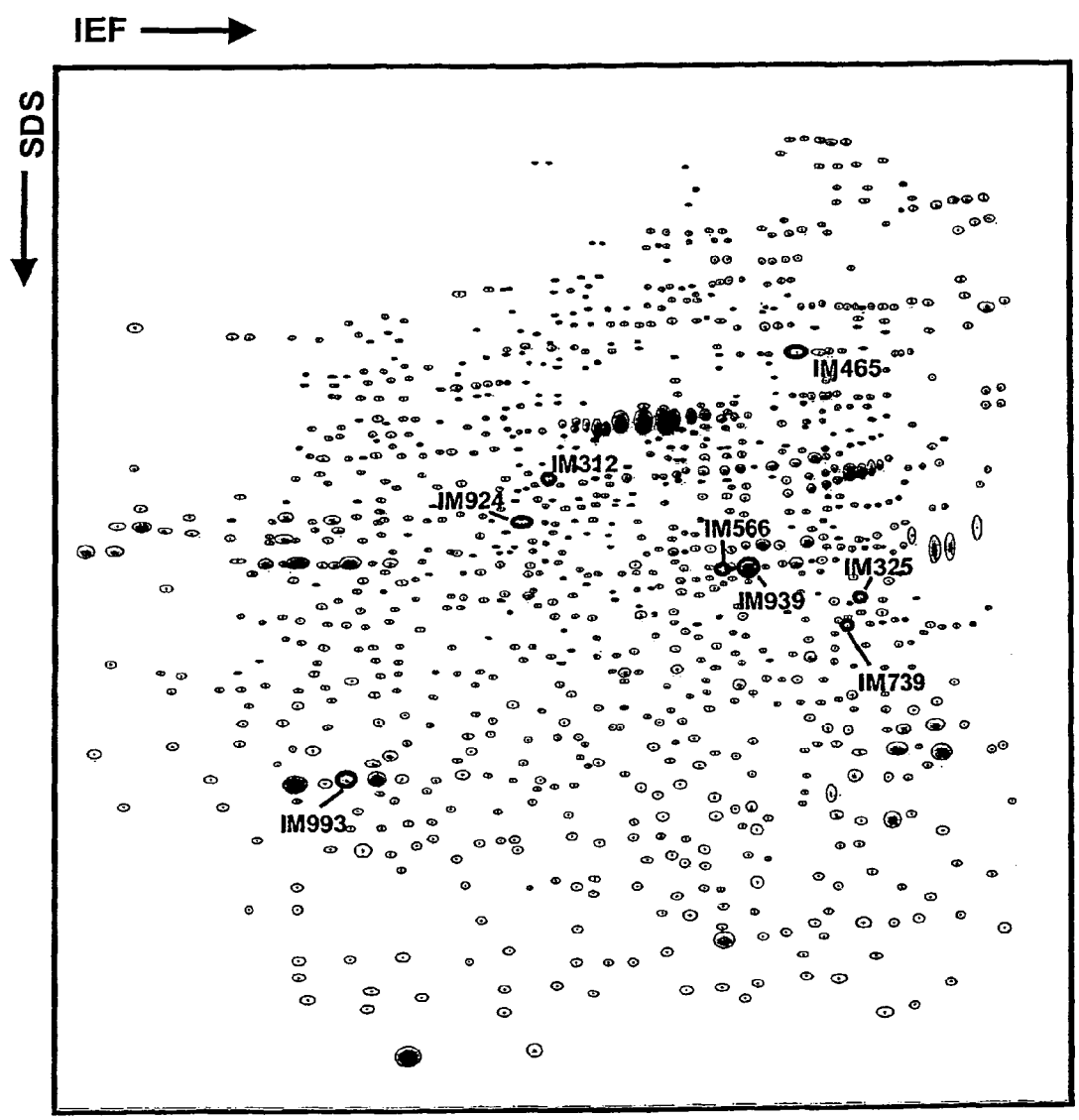

FIG. 4: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with increased synthesis in adenocarcinoma are indicated.

Figure 5:
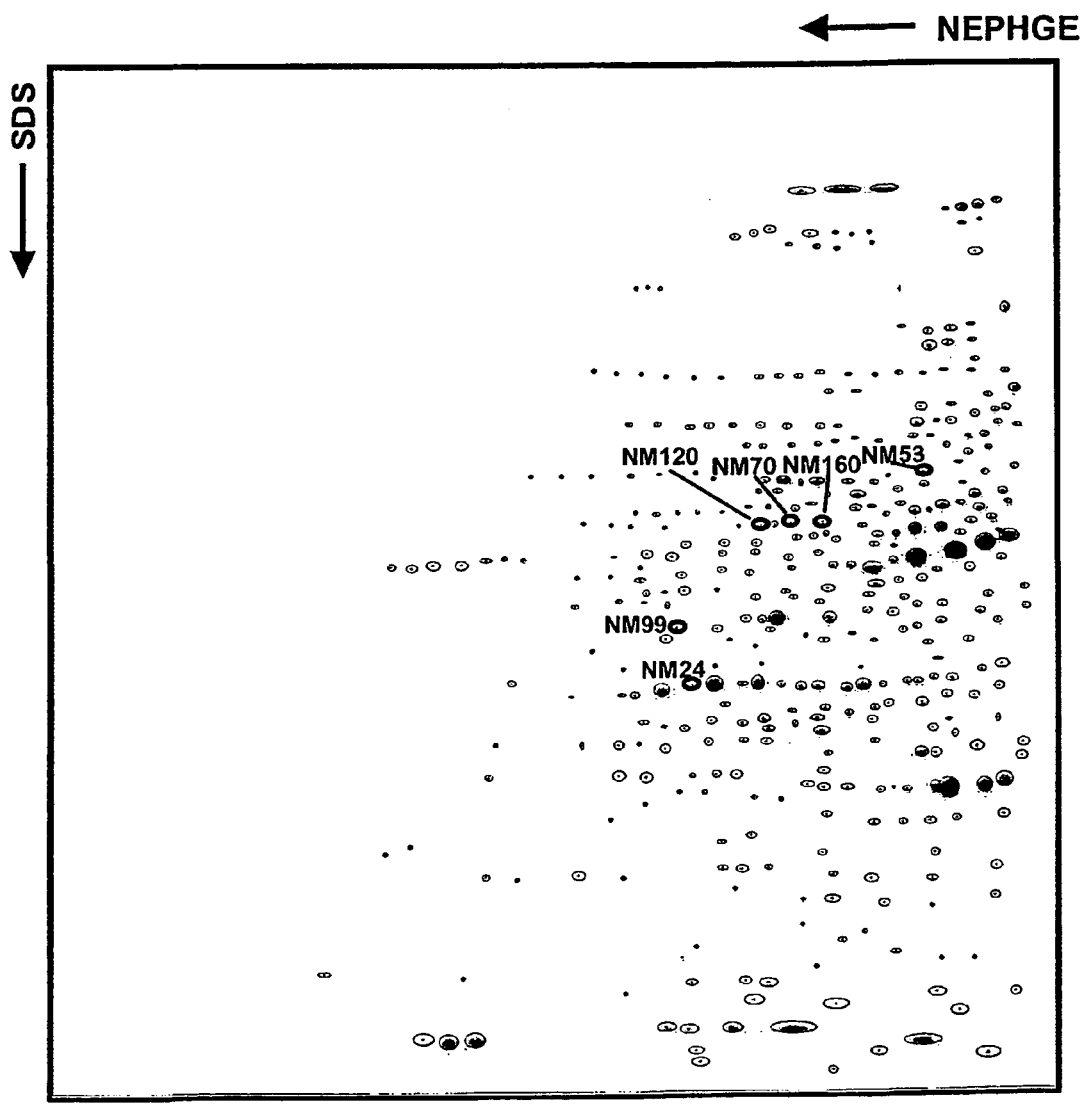

FIG. 5: Phosphoimage composite of two-dimensional gel electrophoresis of [$^{35}$S]methionine labelled endometrial proteins in conditioned medium separated in the first dimension by non-equilibrium pH gradient gel electrophoresis (NEPHGE; pI 6.5-11) and in the second dimension by sodium dodecyl sulphate polyacrylamide gel electrophoresis. The locations of the spots with increased synthesis in adenocarcinoma are indicated.

Figure 6:
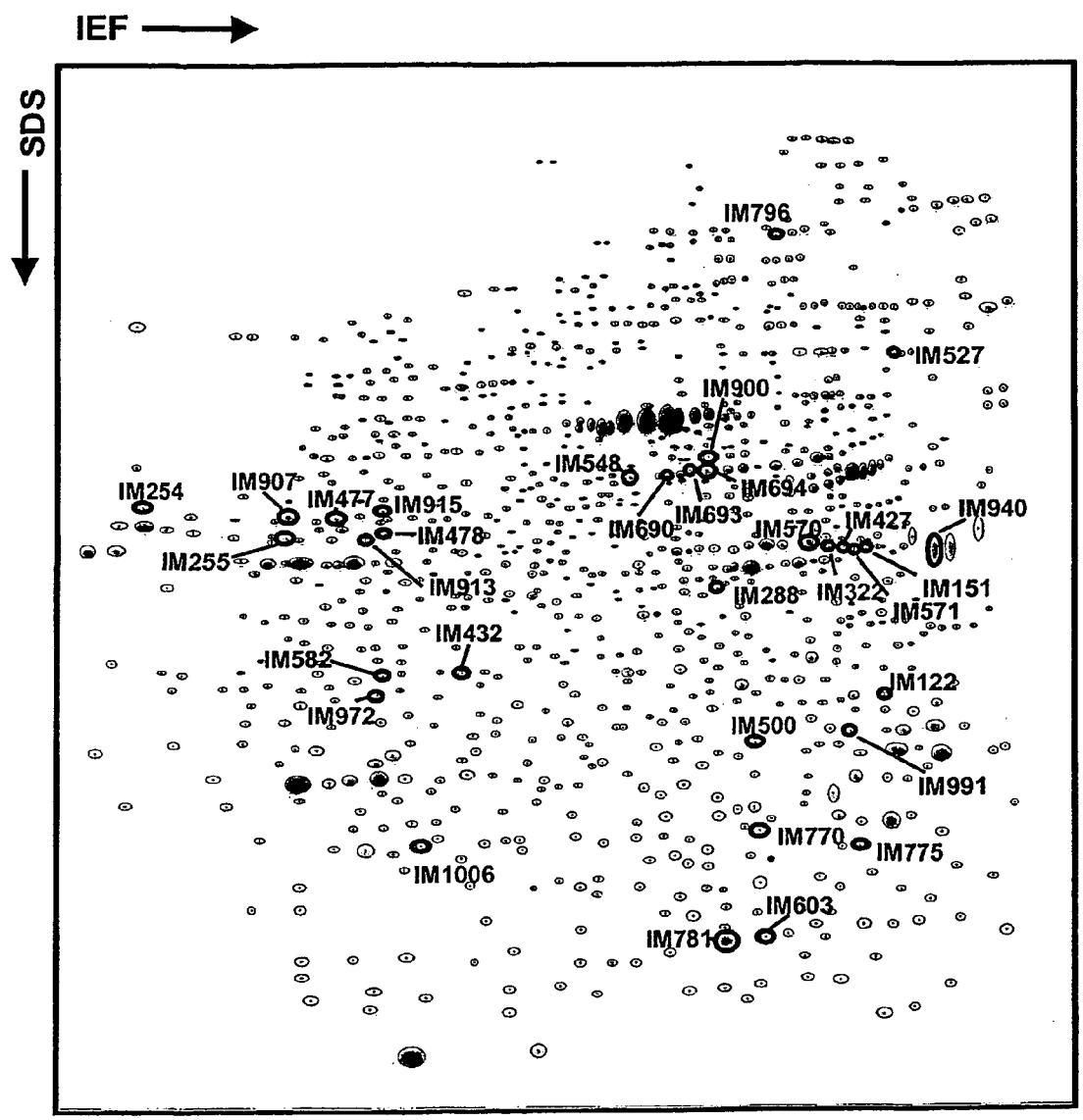

FIG. 6: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with decreased synthesis in adenocarcinoma are indicated.

Figure 7:
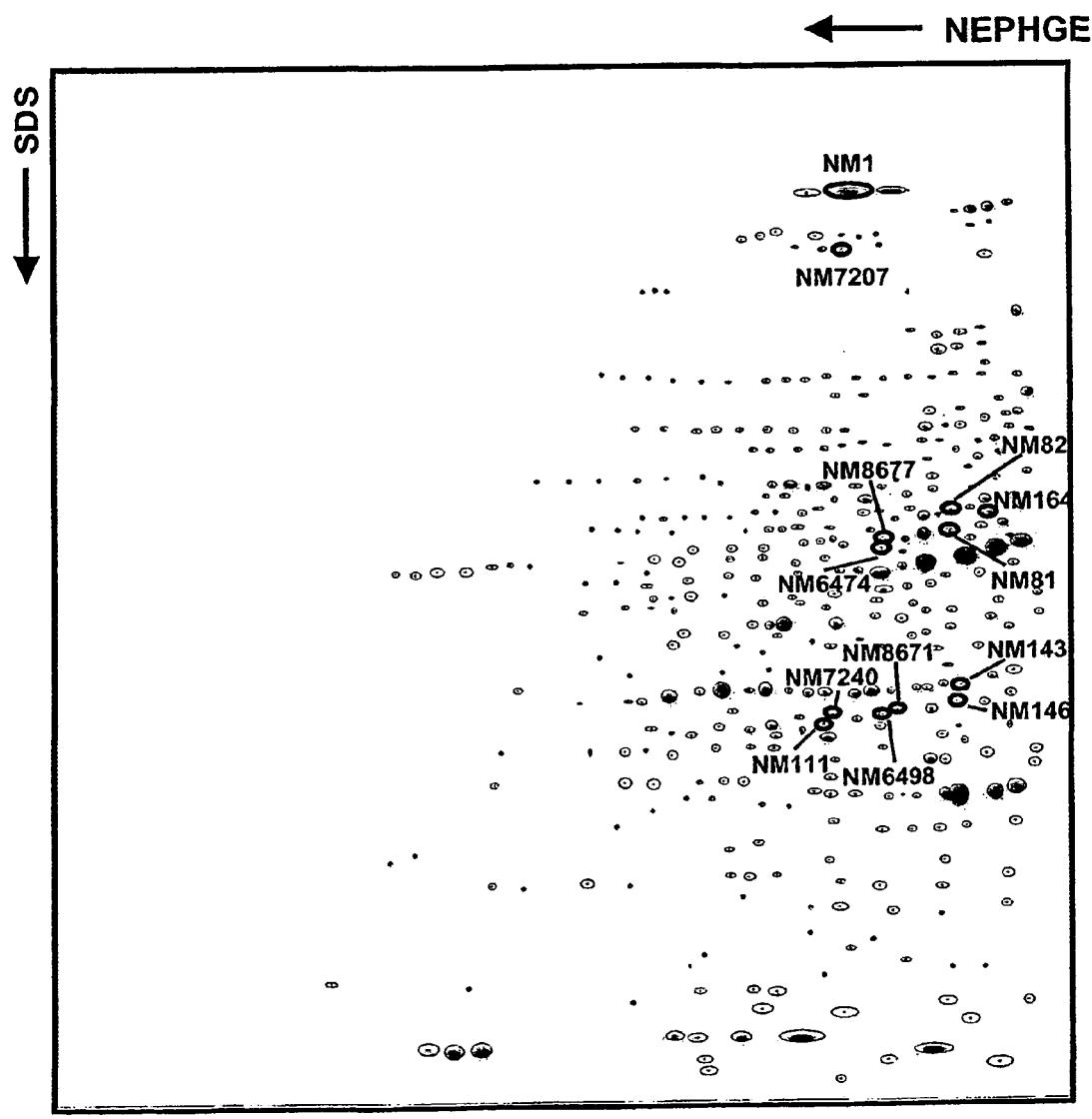

FIG. 7: Phosphoimage composite of two-dimensional gel electrophoresis of [$^{35}$S]methionine labelled-endometrial proteins in conditioned medium separated in the first dimension by non-equilibrium pH gradient gel electrophoresis (NEPHGE; pI 6.5-11) and in the second dimension by sodium dodecyl sulphate polyacrylamide gel electrophoresis. The locations of the spots with decreased synthesis in adenocarcinoma are indicated.

Figure 8:
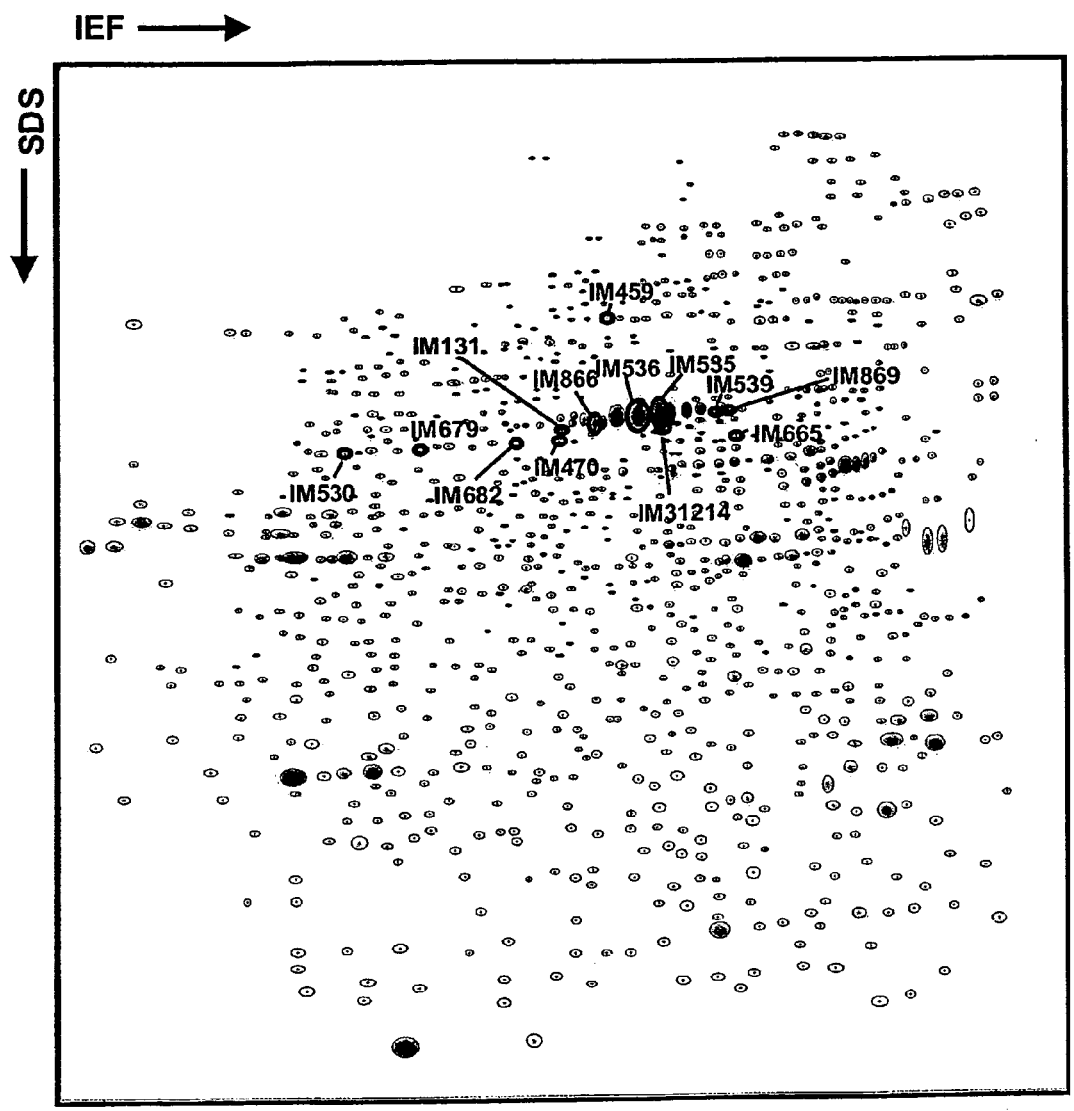

FIG. 8: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with increased synthesis in hyperplasia and adenocarcinoma are indicated.

Figure 9:
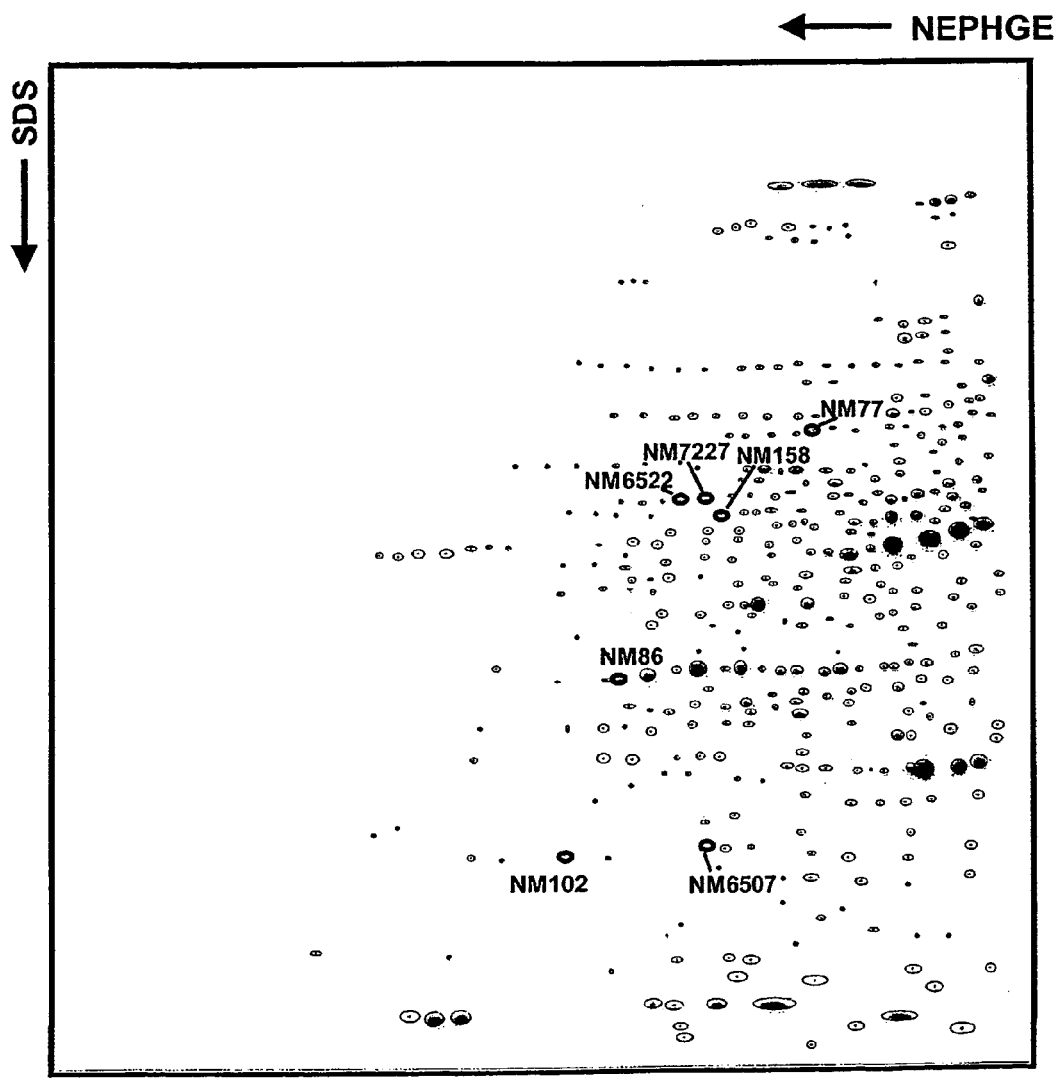

FIG. 9: Phosphoimage composite of two-dimensional gel electrophoresis of [$^{35}$S]methionine labelled endometrial proteins in conditioned medium separated in the first dimension by non-equilibrium pH gradient gel electrophoresis (NEPHGE; pI 6.5-11) and in the second dimension by sodium dodecyl sulphate polyacrylamide gel electrophoresis. The locations of the spots with increased synthesis in hyperplasia and adenocarcinoma are indicated.

Figure 10:
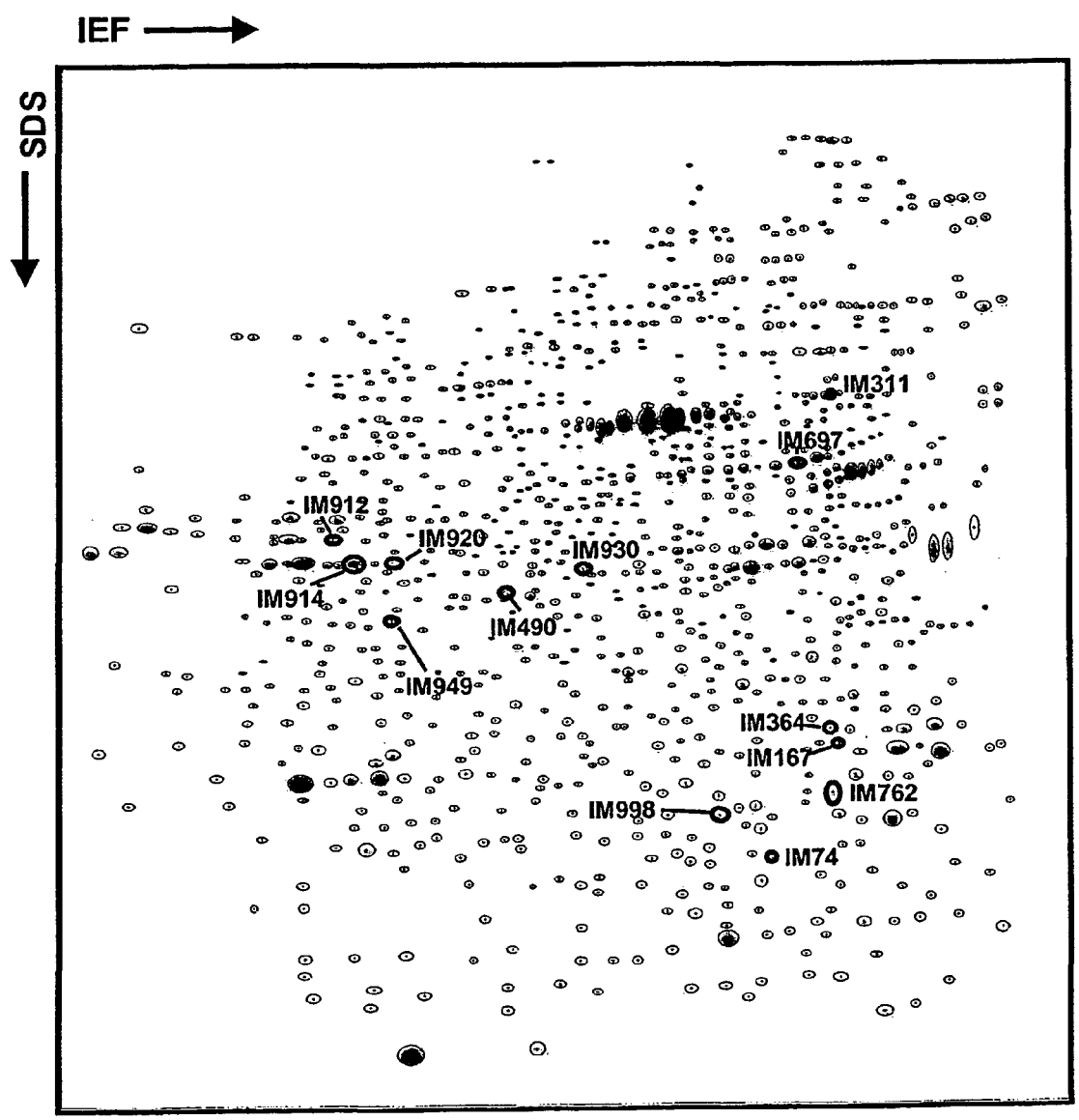

FIG. 10: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with decreased synthesis in hyperplasia and adenocarcinoma are indicated.

Figure 11:
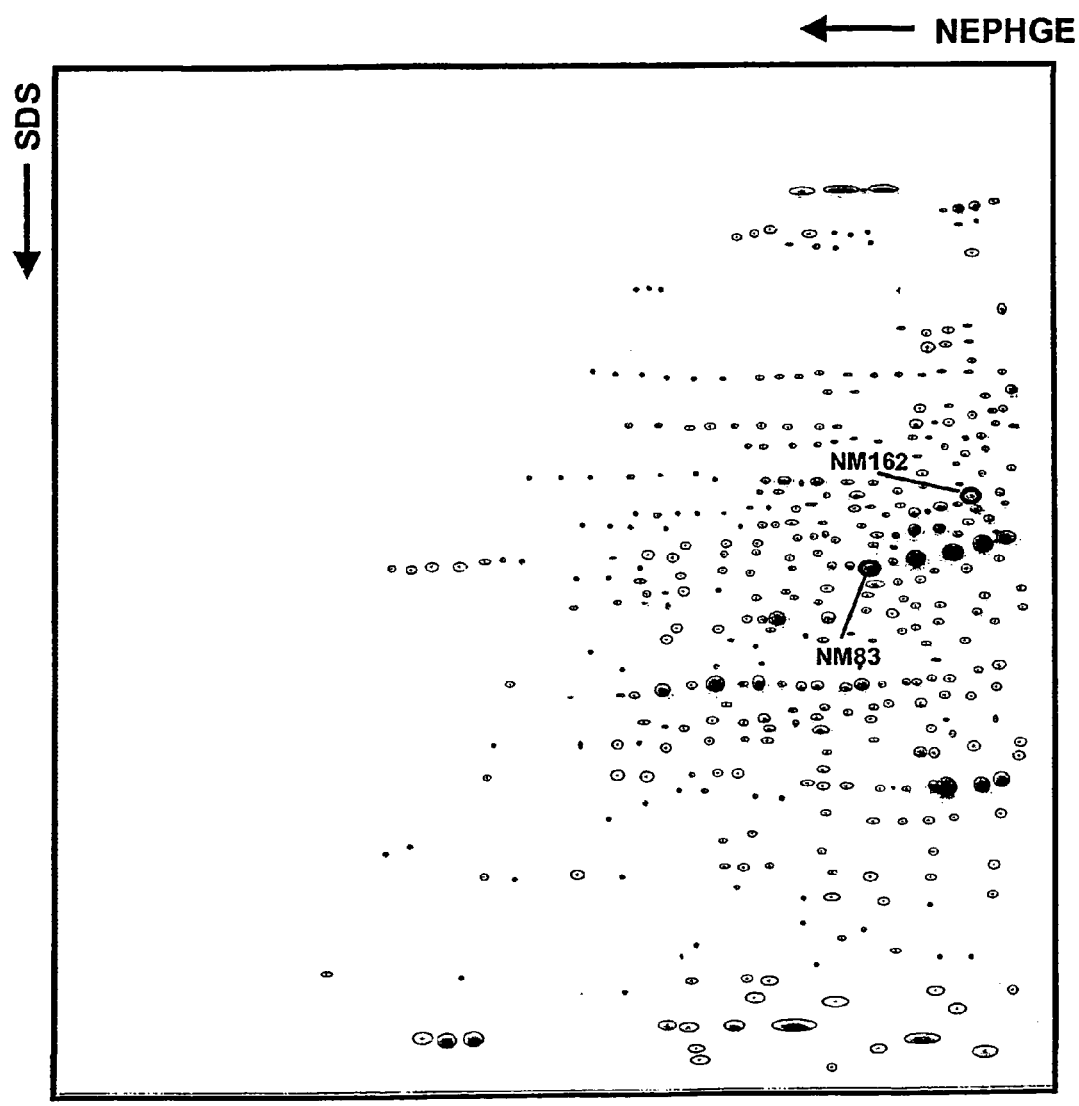

FIG. 11. Phosphoimage composite of two-dimensional gel electrophoresis of [$^{35}$S]methionine labelled endometrial proteins in conditioned medium separated in the first dimension by non-equilibrium pH gradient gel electrophoresis (NEPHGE; pI 6.5-11) and in the second dimension by sodium dodecyl sulphate polyacrylamide gel electrophoresis. The locations of the spots with decreased synthesis in hyperplasia and adenocarcinoma are indicated.

Figure 12:
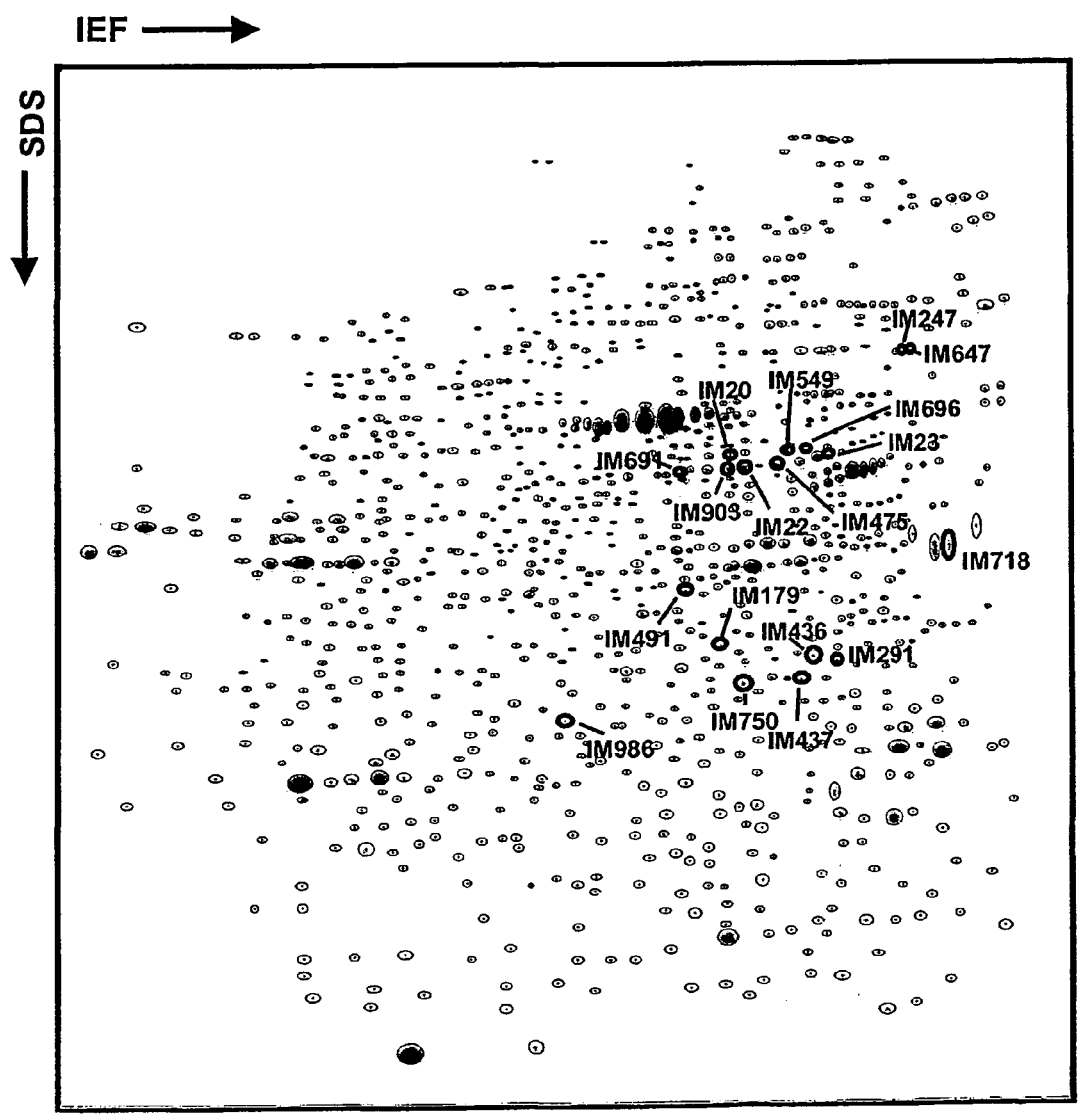

FIG. 12: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with increased synthesis in proliferative phase endometrium are indicated.

Figure 13:
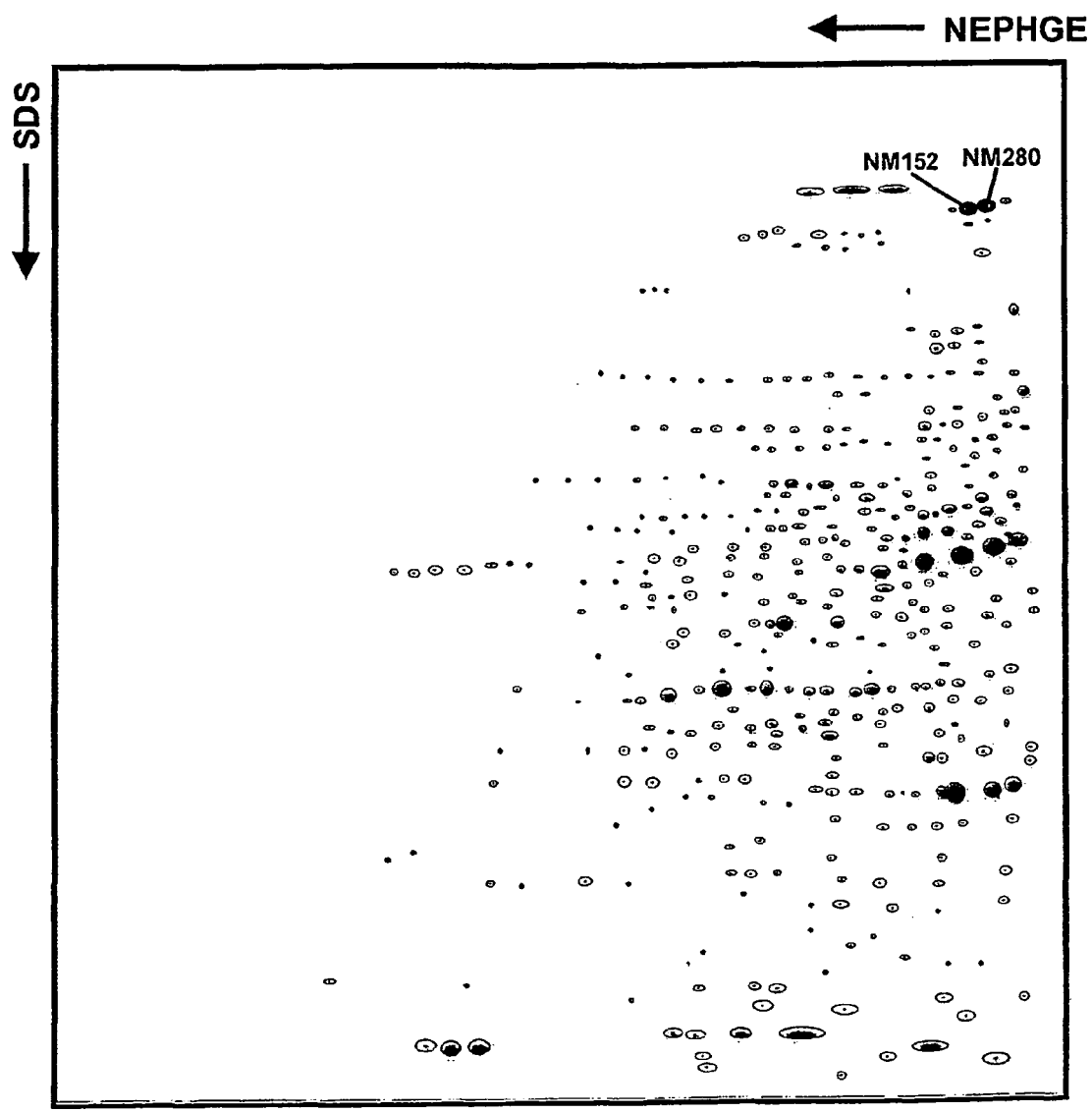

FIG. 13: Phosphoimage composite of two-dimensional gel electrophoresis of [$^{35}$S]methionine labelled endometrial proteins in conditioned medium separated in the first dimension by non-equilibrium pH gradient gel electrophoresis (NEPHGE; pI 6.5-11) and in the second dimension by sodium dodecyl sulphate polyacrylamide gel electrophoresis. The locations of the spots with increased synthesis in proliferative phase endometrium are indicated.

Figure 14:
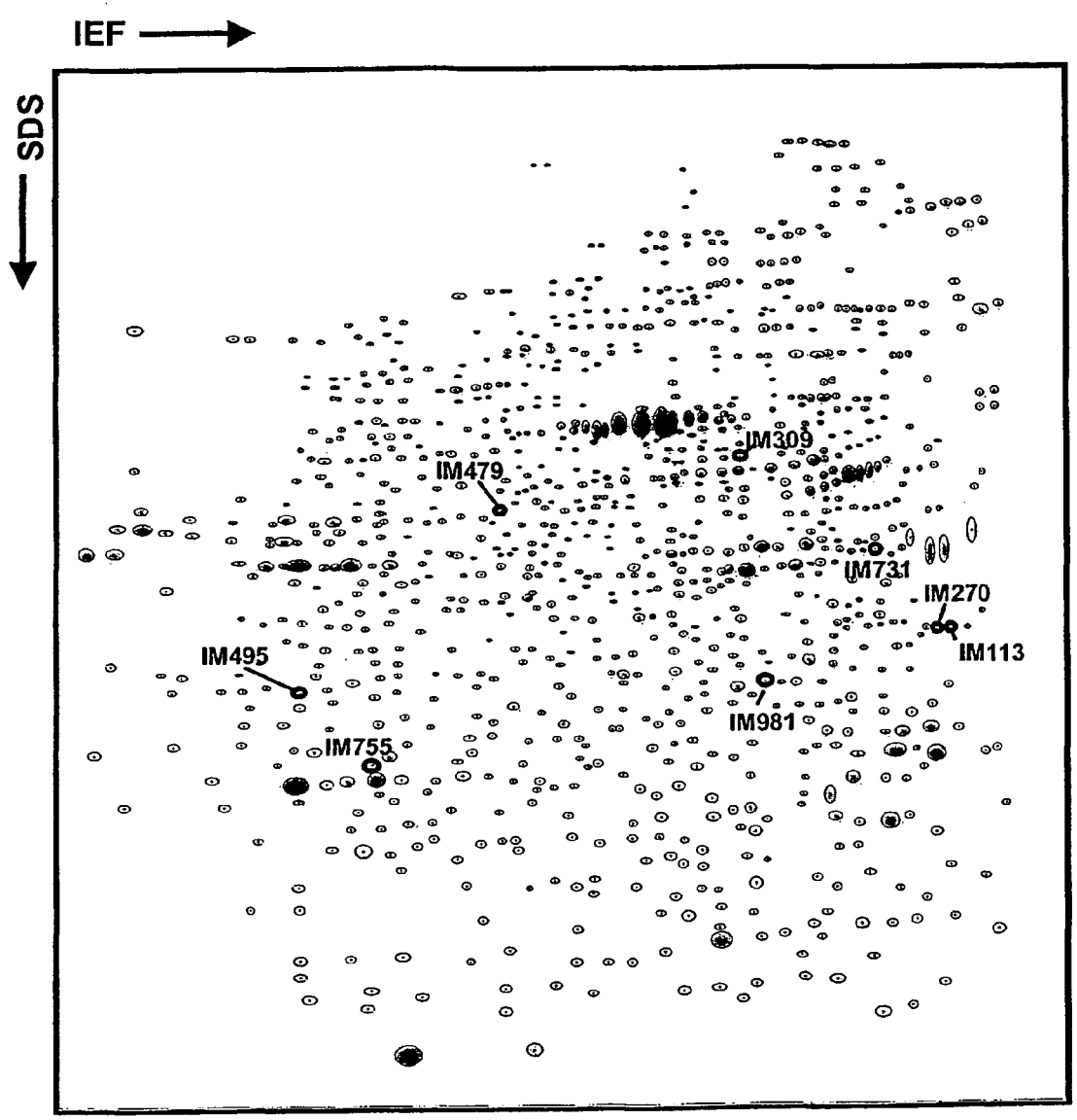

FIG. 14: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with increased synthesis in hyperplasia and proliferative phase endometrium are indicated.

Figure 15:
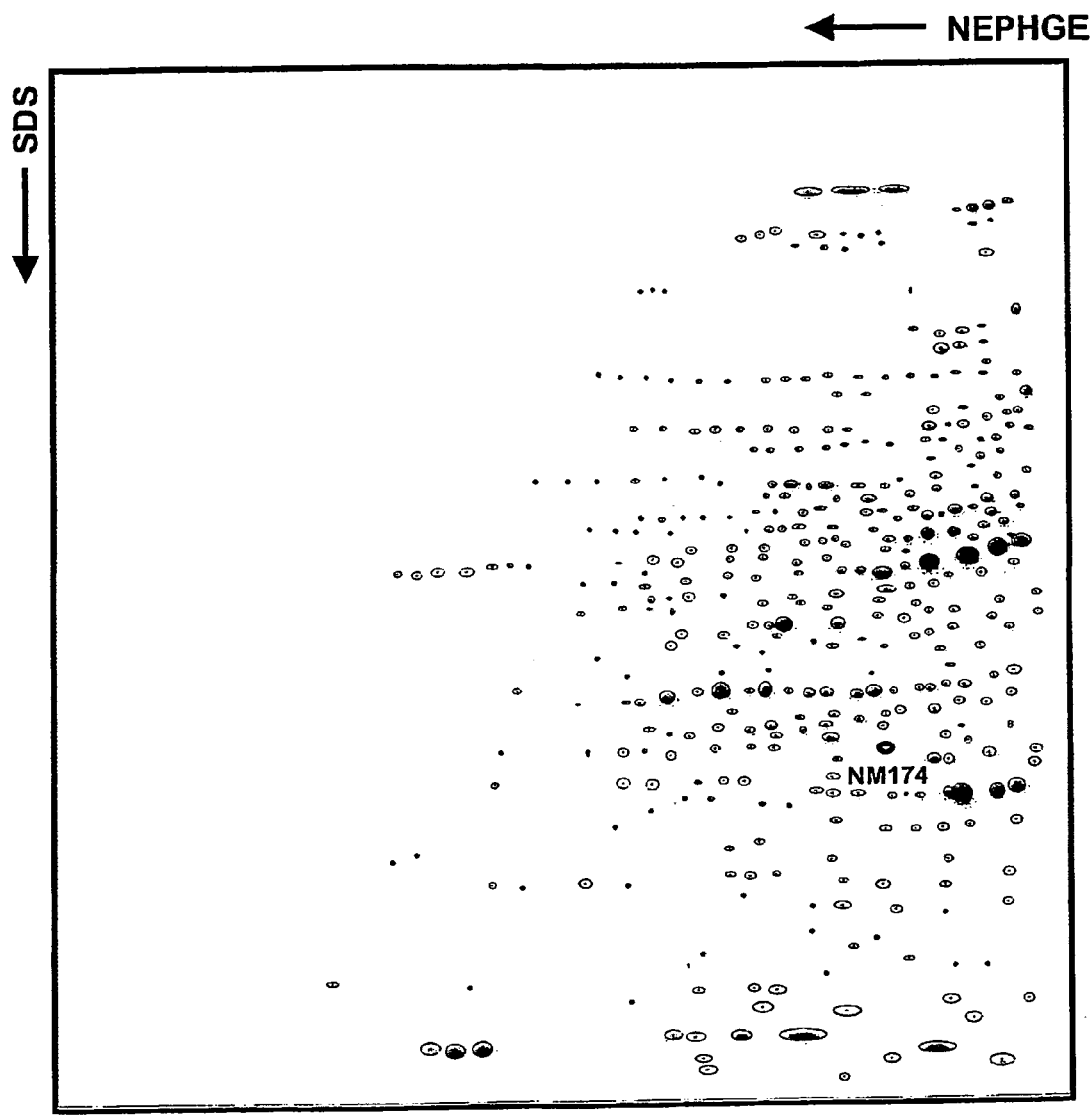

FIG. 15: Phosphoimage composite of two-dimensional gel electrophoresis of [$^{35}$S]methionine labelled endometrial proteins in conditioned medium separated in the first dimension by non-equilibrium pH gradient gel electrophoresis (NEPHGE; pI 6.5-11) and in the second dimension by sodium dodecyl sulphate polyacrylamide gel electrophoresis. The location of the spot with increased synthesis in hyperplasia and proliferative phase endometrium is indicated.

Figure 16:
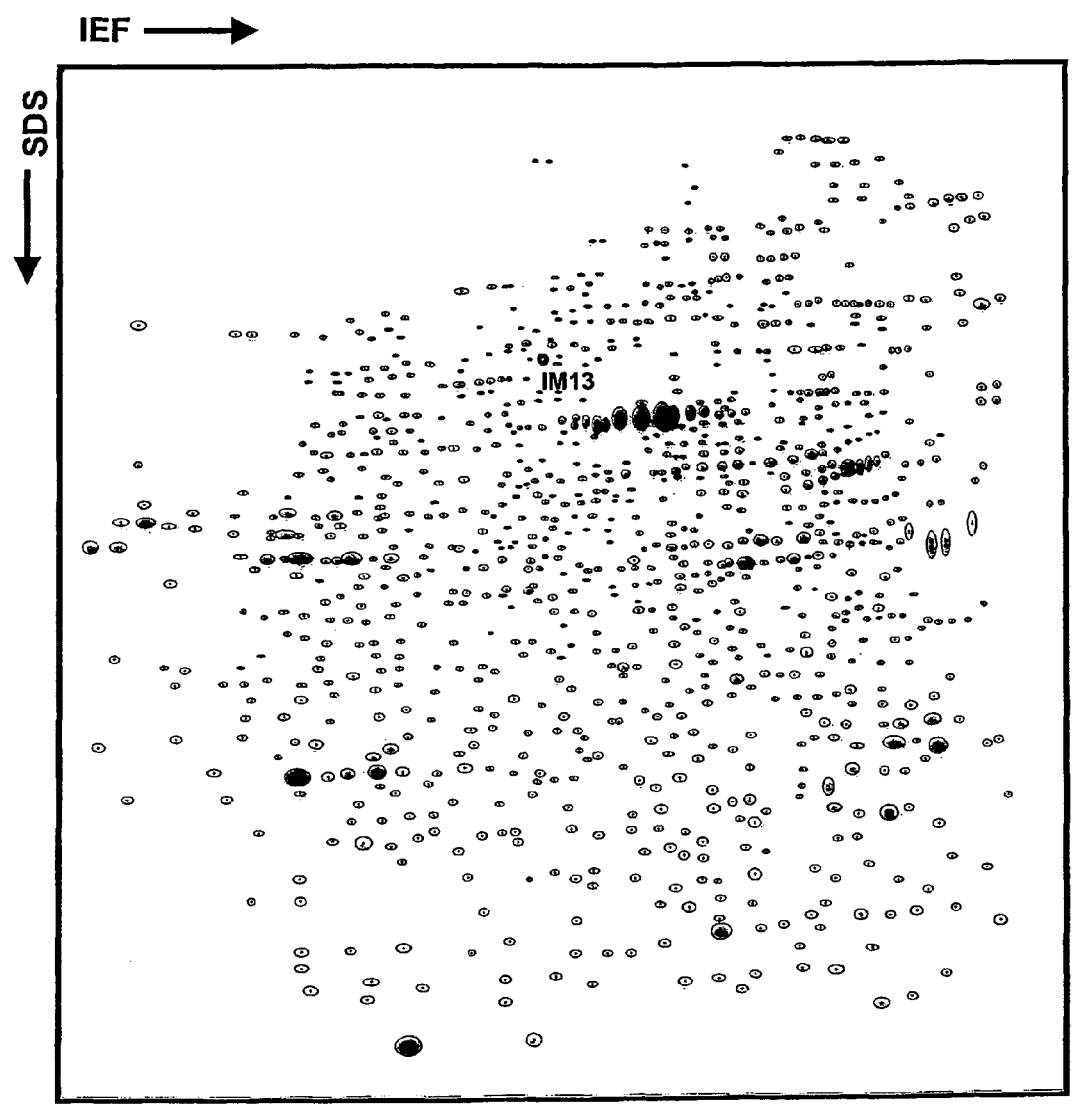

FIG. 16: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The location of the spot with decreased synthesis in proliferative phase endometrium is indicated.

Figure 17:
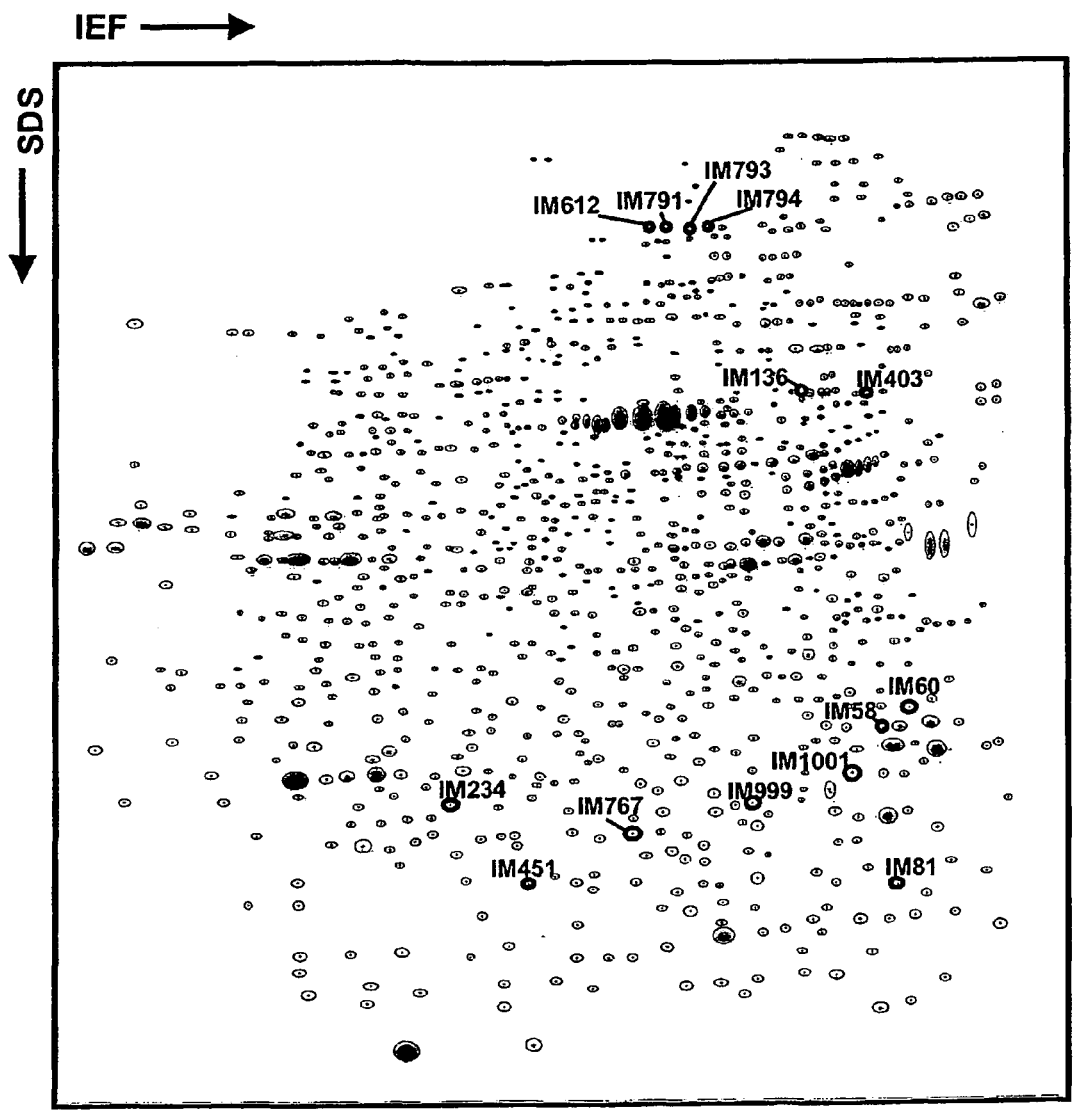

FIG. 17: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with increased synthesis in secretory phase endometrium are indicated.

Figure 18:
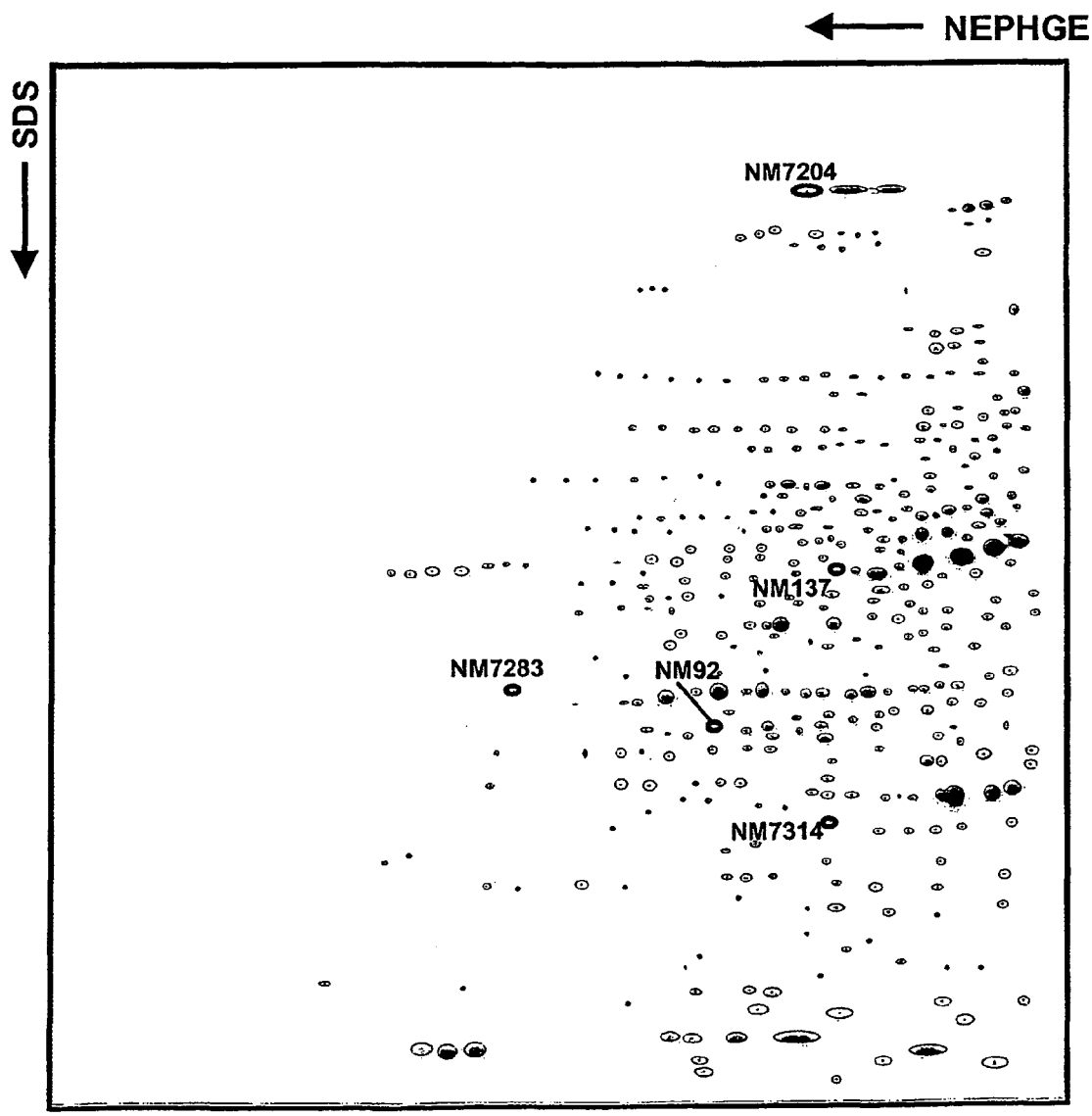

FIG. 18: Phosphoimage composite of two-dimensional gel electrophoresis of [$^{35}$S]methionine labelled endometrial proteins in conditioned medium separated in the first dimension by non-equilibrium pH gradient gel electrophoresis (NEPHGE; pI 6.5-11) and in the second dimension by sodium dodecyl sulphate polyacrylamide gel electrophoresis. The locations of the spots with increased synthesis in secretory phase endometrium are indicated.

Figure 19:
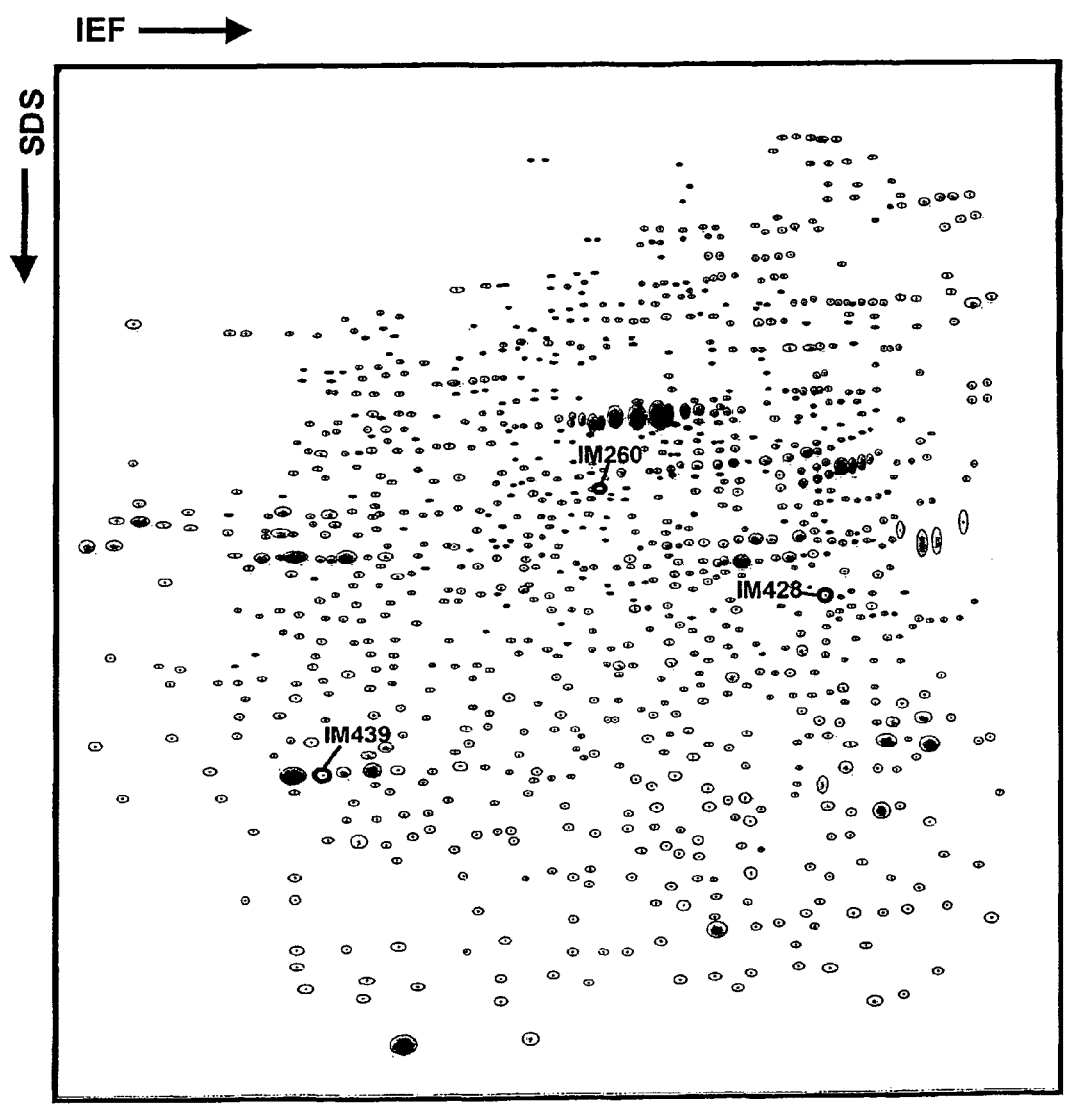

FIG. 19: Phosphoimage composite of two-dimensional gel electrophoresis of [$^{35}$S]methionine labelled endometrial proteins in conditioned medium separated in the first dimension by iso-electric focusing (IEF; pI 3.5-7) and in the second dimension by sodium dodecyl sulphate polyacrylamide gel electrophoresis. The locations of the spots with decreased synthesis in secretory phase endometrium are indicated.

Figure 20:
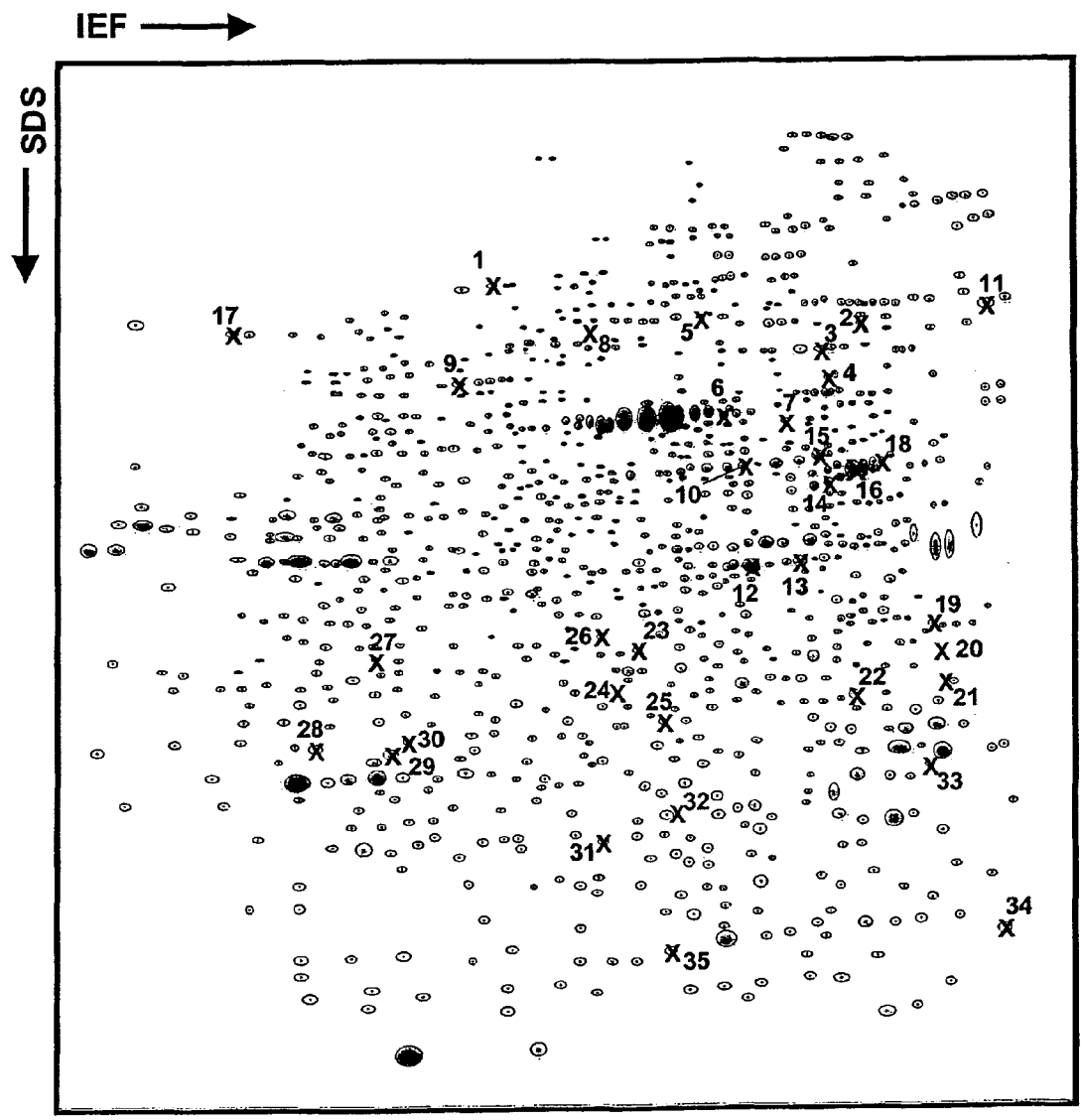

FIG. 20: Phosphoimage composite of 2D gel electrophoresis of [$^{35}$S] methionine labelled standards and endometrial proteins in conditioned medium separated in the first dimension by iso-electric focusing (IEF;pI 3.5-7) and in the second dimension by sodium dodecyl sulphate polyacrylamide gel electrophoresis. The locations of the standards are marked.

Figure 21:
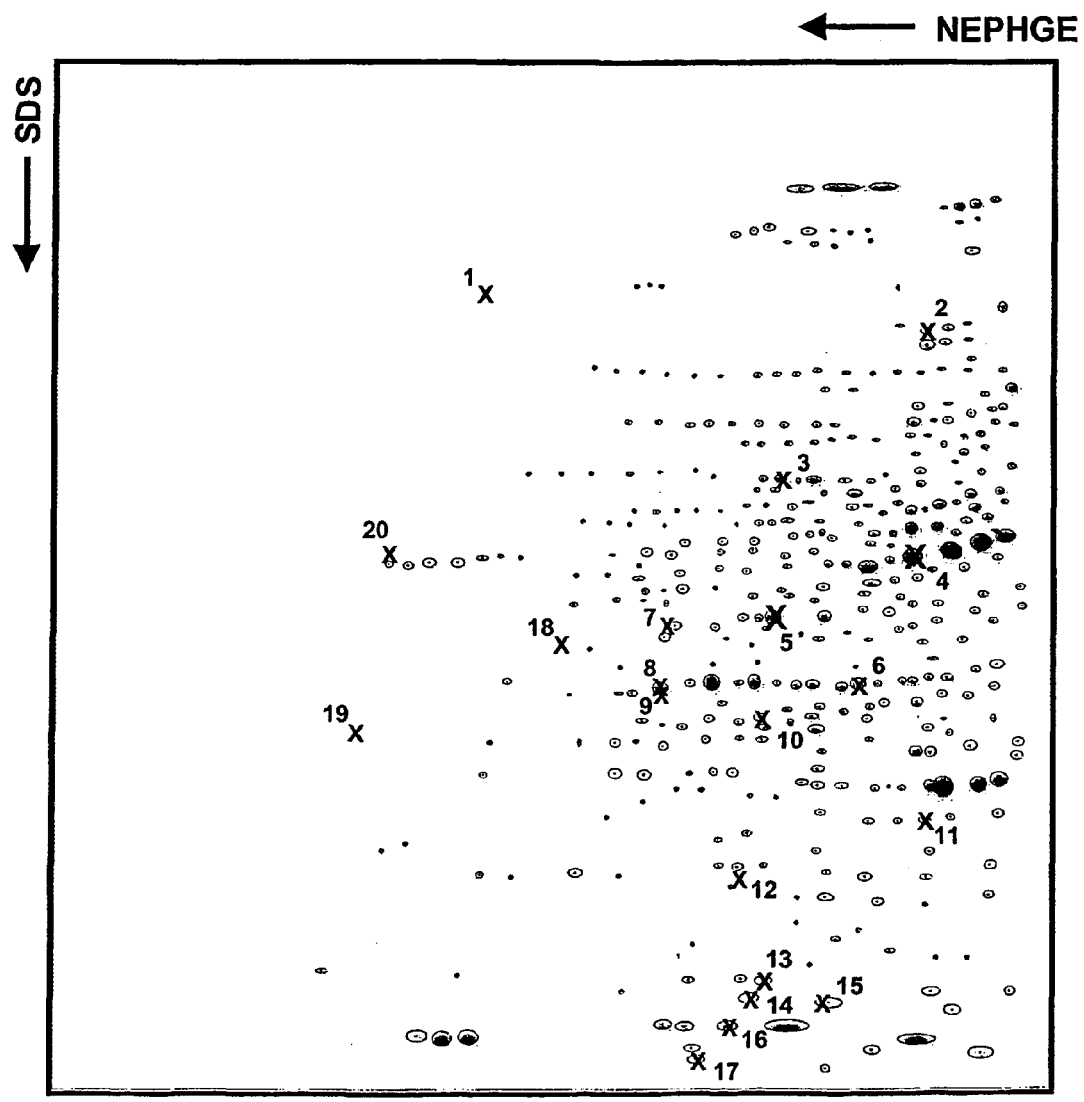

FIG. 21: Phosphoimage composite of 2D gel electrophoresis of [$^{35}$S] methionine labelled standards and endometrial proteins in conditioned medium separated in the first dimension by non-equilibrium pH gradient gel electrophoresis (NEPHGE; pI 6.5-11) and in the second dimensions by sodium dodecyl sulphate polyacrylamide gel electrophoresis. The locations of the standards are marked.

FIG. 22: Peptide mass fingerprint spectrum of tryptic digest of IM718. The protein specific peaks are marked with their m/z-value [MH+]. The non-marked peaks represents methodologically non-specific peaks.

To identify proteins or polypeptides expressed at an increased level in differing endometrial conditions, endometrial samples were obtained as follows.

Endometrial biopsies were collected from 58 women (35-95 years of age) undergoing endometrial curettage (n=9) or hysterectomy (removal of the uterus) (n=49). Based on the histological evaluation of the endometrial biopsies the patients were assigned to one of four groups having proliferative phase endometrium (n=18); secretory phase endometrium (n=18); endometrial hyperplasia (n=9), or endometrial adenocarcinoma (n=13). The samples were treated as described in Ref. 1. The proteins of the endometrial biopsies were metabolically labelled with $^{35}$S-methionine for 20 hours, and the conditioned media of these endometrial biopsy explants were processed for 2D gel electrophoresis, a technique in which proteins are separated in the first dimension according to the isoelectric point and in the second dimension according to the molecular weight. It was possible to study proteins with iso-electric points ranging from 3.5 to 11 and relative molecular weights ranging from 10 to 300 kDa. After electrophoresis the gels were fixed and treated for phosphoimage development. The phosphoimage images of the 2D gel electrophoresis were subjected to quantitative analysis by computer-aided analysis, by which the density of each spot was quantified; the phosphoimage patterns were matched i.e. numbers were assigned to each spot and the same spot was given the same number on all the images. The density (quantitated synthesis) of each spot was statistically assessed using non-parametric analysis of variance (Kruskal-Wallis test; a p-value of 0.05 or less was considered as significant) to find proteins with regulated synthesis in the endometrial tissue explant culture media. The regulation pattern of the proteins having a statistically significant synthesis was assessed to find proteins with increased synthesis in endometrial hyperplasia or adenocarcinoma, and proteins with decreased synthesis in endometrial hyperplasia or adenocarcinoma, and proteins with increased synthesis in proliferative phase endometrium as compared to secretory phase endometrium and hyperplasia and adenocarcinoma; and proteins with increased synthesis in proliferative phase endometrium and hyperplasia as compared to secretory phase endometrium and adenocarcinoma; and proteins with decreased synthesis in proliferative phase endometrium as compared to secretory phase endometrium and hyperplasia and adeno-carcinoma; and proteins with increased synthesis in secretory phase endometrium as compared to proliferative phase endo-metrium and hyperplasia and adenocarcinoma; and proteins with decreased synthesis as compared to proliferative phase endometrium and hyperplasia and adenocarcinoma. Spots related to such proteins are marked in the Figures with spot identifier codes. The proteins of the present invention that show a regulated synthesis associated with the endometrial histology, may be identified by amino acid sequence analysis or by peptide mass fingerprinting analysis.

In detail, the intensity of the spots was analysed as follows.

First the data was statistically analysed to find the spots having a differential expression among the four histologically defined groups of proliferative phase endometrium, secretory phase endometrium, endometrial hyperplasia, and endometrial cancer (Kruskal-Wallis non-parametric analysis of variance for each of the proteins; significance level $p<0.05$).

In sub-set of data with statistically significant analysis of variance was then analysed by a non-parametric two level test (Wilcoxon) for each of the proteins to assess whether it could be assumed that the expression in proliferative phase endometrium was comparable with the expression in secretory phase endometrium (significance level $p<0.05$).

For the group of proteins with expression not being different in these two normal conditions (i.e. $p>=0.05$), the data of proliferative phase and secretory phase was pooled into a group having normal conditions of the endometrium. A non-parametric two-level test (Wilcoxon) was then performed to assess whether the expression in hyperplasia could be assumed to be comparable with the expression in the normal conditions, and whether the expression in cancer could be assumed to be comparable with the expression in the normal conditions. These statistical analysis was the basis to select the proteins having increased/decreased expression in hyperplasia, and/or cancer (significance level 0.05).

For the group of proteins with different expression in proliferative phase and secretory phase endometrium, the data of hyperplasia was compared with each of these normal conditions, and the data of cancer was compared with each of these normal conditions (non-parametric two-level test, Wilcoxon, significance level $p<0.05$).

Next for each of the regulated proteins (statistically significant analysis of variance) a figure was drawn of the expression of the individual patient sample grouped into the four histologically defined group.

Based on the statistical analysis (significant or borderline significant), subjective visual assessment of the expression pattern, and evaluation of the expression pattern from a practical point of view (clinical usefulness), the regulated proteins were classified into the various categories. From the regulated proteins, several were selected for use in assay procedures according to the invention. These are detailed in the following tables which are further described below:

TABLE 1

Endometrial proteins with increased synthesis in hyperplasia

| Spot ID | Identifier | Protein name | Observed MW ± 10% (kDa) | Observed pI ± 0.25 |
|---|---|---|---|---|
| IM285 | | | 44.2 | 5.5 |
| IM515 | sp\|P07476 | Involucrin | 124.1 | 4.6 |
| IM660 | sp\|P38646 | Mortalin-2 | 66.2 | 5.3 |
| NM75 | | | 20.8 | 7.9 |

TABLE 2

Endometrial proteins with decreased synthesis in hyperplasia

| Spot ID | Identifier | Protein name | Observed MW ± 10% (kDa) | Observed pI ± 0.25 |
|---|---|---|---|---|
| IM997 | | | 24.4 | 5.3 |

TABLE 3

Endometrial proteins with increased synthesis in adenocarcinoma

| Spot ID | Identifier | Protein name | Observed MW ± 10% (kDa) | Observed pI ± 0.25 |
|---|---|---|---|---|
| IM312 | sp\|P17987 | T-complex polypeptide 1 | 55.7 | 5.8 |
| IM465 | sp\|P07900 | Heat shock protein HSP-90 beta | 82.1 | 4.9 |
| IM924 | sp\|Q08945 | Structure specific recognition protein 1 fragment including at least residues: 37-413 | 50.4 | 5.9 |
| IM939 | sp\|P04270 sp\|P02570 sp\|P02571 | α, β, or γ-actin | 43.8 | 5.1 |
| IM993 | pir\|I59377 | Template activating factor-1, alpha | 26.6 | 6.5 |
| NM53 | | | 62.6 | 7.4 |
| NM99 | sp\|P17936 | Insulin-like growth factor binding protein 3 | 43.1 | 8.6 |
| NM120 | sp\|Q92841 | DEAD/H box polypeptide 17 fragment including at least residues: 30-449 | 53.6 | 8.3 |

TABLE 4

Endometrial proteins with decreased synthesis in adenocarcinoma

| Spot ID | Identifier | Protein name | Observed MW ± 10% (kDa) | Observed pI ± 0.25 |
|---|---|---|---|---|
| IM122 | sp\|P02570 sp\|P02571 | β or γ-actin fragment including at least residues: 29-206 | 30.5 | 4.7 |
| IM151 | | | 46.6 | 4.7 |
| IM254 | sp\|P00367 | Glutamate dehydrogenase | 57.6 | 6.9 |
| IM255 | | | 52.1 | 6.6 |
| IM288 | sp\|Q9UJZ1 | Stomatin like protein 2 | 42.0 | 5.3 |
| IM427 | | | 46.8 | 4.8 |
| IM432 | sp\|P04083 | Annexin I | 34.8 | 6.1 |
| IM478 | | | 50.0 | 6.4 |
| IM500 | | | 28.0 | 5.2 |
| IM527 | | | 86.2 | 4.6 |
| IM548 | gi\|5803113 | Transmembrane protein ER | 55.5 | 5.6 |
| IM570 | sp\|p07711 | Cathepsin L | 47.2 | 5.0 |
| IM571 | | | 46.5 | 4.8 |
| IM582 | sp\|P04083 | Annexin 1 | 34.5 | 6.3 |
| IM690 | sp\|O43390 | Heterogeneous nuclear ribonucleoprotein R | 55.5 | 5.5 |
| IM693 | sp\|P50990 | Chaperonin containing TCP1 subunit 8 | 56.2 | 5.4 |
| IM694 | sp\|P50990 | Chaperonin containing TCP1 subunit 8 | 56.0 | 5.3 |
| IM770 | | | 22.0 | 5.2 |
| IM775 | | | 20.0 | 4.8 |
| IM781 | | | 15.4 | 5.3 |
| IM796 | sp\|Q9Y4L1 | Oxygen related protein | 139.4 | 5.0 |
| IM900 | | | 57.8 | 5.3 |
| IM907 | | | 55.5 | 6.6 |
| IM913 | | | 50.0 | 6.4 |
| IM915 | | | 53.3 | 6.3 |
| IM940 | | | 46.3 | 4.4 |
| IM972 | sp\|P04083 | Annexin 1 | 32.7 | 6.3 |
| IM991 | | | 28.3 | 4.8 |
| IM1006 | | | 23.8 | 6.3 |
| NM1 | sp\|O75334 | Liprin-alpha 2 | 130.7 | 7.7 |
| NM81 | sp\|P00367 | Glutamate dehydrogenase | 55.3 | 7.3 |
| NM82 | sp\|P00367 | Glutamate dehydrogenase | 58.2 | 7.3 |
| NM111 | sp\|P00338 | L-Lactate dehydrogenase M chain | 35.1 | 7.9 |
| NM143 | sp\|P07355 | Annexin II | 39.8 | 7.2 |
| NM146 | sp\|P40925 | Malate dehydrogenase, cytoplasmic | 38.4 | 7.2 |
| NM6498 | | | 36.9 | 7.6 |
| NM7207 | | | 111.0 | 7.8 |
| NM7240 | | | 36.0 | 7.9 |
| NM8671 | | | 37.3 | 7.5 |

TABLE 5

Endometrial proteins with increased synthesis in hyperplasia and adenocarcinoma

| Spot ID | Identifier | Protein name | Observed MW ± 10% (kDa) | Observed pI ± 0.25 |
|---|---|---|---|---|
| IM131 | | | 61.6 | 5.8 |
| IM459 | sp\|O43707 | Actinin, alpha 4 | 92.5 | 5.5 |
| IM470 | sp\|P31948 | Stress induced phosphoprotein 1 | 60.0 | 5.8 |
| IM530 | sp\|311948 + sp\|P31939 | Stress induced phoshoprotein 1 + purH | 62.8 | 6.4 |
| IM535 | | | 63.5 | 5.4 |
| IM536 | | | 63.2 | 5.5 |
| IM665 | | | 60.6 | 5.2 |
| IM679 | sp\|P31948 | Stress induced phosphoprotein 1 | 59.7 | 6.2 |
| IM682 | sp\|P31948 | Stress induced phosphoprotein 1 | 59.9 | 5.9 |
| IM866 | | | 62.5 | 5.7 |
| NM77 | sp\|P52272 | Heterogeneous nuclear ribonucleoprotein M | 65.5 | 7.9 |
| NM158 | sp\|Q92841 | DEAD/H box polypeptide 17 fragment including at least residues: 30-449 | 53.5 | 8.4 |
| NM6507 | sp\|Q06830 | Peroxiredoxin 1 | 23.1 | 8.4 |
| NM6522 | | | 55.9 | 8.5 |
| NM7227 | | | 55.4 | 8.4 |

TABLE 6

Endometrial proteins with decreased synthesis in hyperplasia and adenocarcinoma

| Spot ID | Identifier | Protein name | Observed MW ± 10% (kDa) | Observed pI ± 0.25 |
|---|---|---|---|---|
| IM74 | | | 20.1 | 5.2 |
| IM167 | sp\|P08729 | Keratin 7 fragment including at least residues: 52-225 | 27.4 | 4.9 |
| IM311 | | | 67.7 | 4.8 |
| IM364 | sp\|P02570 sp\|P02571 | β or γ-actin fragment including at least residues: 29-206 | 28.6 | 4.9 |
| IM490 | | | 42.4 | 6.0 |
| IM697 | sp\|Q9NY65 | Tubulin, alpha 8 | 58.5 | 5.0 |
| IM762 | | | 24.1 | 4.9 |
| IM912 | gi\|13630152 | Hypothetical protein FLJ10849 | 51.4 | 6.5 |
| IM920 | | | 46.2 | 6.3 |
| IM930 | | | 45.0 | 5.8 |
| IM949 | | | 39.6 | 6.4 |
| IM998 | | | 23.2 | 5.3 |
| NM162 | sp\|Q9GZM7 | P3ECSL | 60.4 | 7.1 |

TABLE 7

Endometrial proteins with increased synthesis in proliferative phase endometrium

| Spot ID | Identifier | Protein name | Observed MW ± 10% (kDa) | Observed pI ± 0.25 |
|---|---|---|---|---|
| IM20 | | | 57.8 | 5.2 |
| IM22 | sp\|P10809 | 60 kDA Heat shock protein | 56.2 | 5.2 |
| IM23 | gi\|3420929 | Tubulin, alpha isoform 1 | 58.3 | 4.9 |
| IM179 | sp\|P30464 | HLA class I histocompatibility antigen, alpha chain | 36.1 | 5.3 |
| IM247 | | | 86.3 | 4.6 |
| IM291 | | | 33.9 | 4.9 |
| IM436 | sp\|Q9BW10 | Tubulin, beta 4 | 34.4 | 4.9 |
| IM437 | | | 32.6 | 5.0 |
| IM475 | | | 57.5 | 5.1 |
| IM491 | sp\|P49903 | Selenophosphate synthetase | 41.9 | 5.4 |
| IM549 | | | 60.6 | 5.0 |
| IM647 | | | 86.4 | 4.5 |
| IM691 | sp\|P50990 | T-complex protein 1, theta subunit | 55.7 | 5.4 |
| IM696 | gi\|12737610 | Keratin 7 | 60.8 | 5.0 |
| IM718 | | Spectrum shown in FIG. 22 | 46.6 | 4.4 |
| IM750 | | | 32.5 | 5.2 |
| IM903 | | | 55.8 | 5.2 |
| IM986 | gi\|1314645 | Cytoplasmic dynein heavy chain 22 fragment including at least residues: 146-273 | 31.9 | 5.8 |
| NM152 | | | 118.6 | 7.5 |
| NM280 | | | 120.0 | 7.4 |

TABLE 8

Endometrial proteins with increased synthesis in hyperplasia and proliferative phase endometrium

| Spot ID | Identifier | Protein name | Observed MW ± 10% (kDa) | Observed pI ± 0.25 |
|---|---|---|---|---|
| IM113 | | | 36.3 | 4.4 |
| IM309 | sp\|O43707 | Actinin, alpha 4 fragment including at least residues: 301-771 | 58.5 | 5.2 |
| IM479 | | | 52.1 | 6.0 |
| IM495 | sp\|P10768 | Esterase D | 32.6 | 6.8 |
| IM731 | | | 46.8 | 4.7 |
| IM755 | | | 27.5 | 6.4 |
| IM981 | sp\|P19623 | Spermidine Synthase | 32.8 | 5.1 |
| NM174 | | | 34.2 | 7.6 |

TABLE 9

Endometrial proteins with decreased synthesis in proliferative phase endometrium

| Spot ID | Identifier | Protein name | Observed MW ± 10% (kDa) | Observed pI ± 0.25 |
|---|---|---|---|---|
| IM13 | | | 76.1 | 5.8 |

TABLE 10

Endometrial proteins with increased synthesis in secretory phase endometrium

| Spot ID | Identifier | Protein name | Observed MW ± 10% (kDa) | Observed pI ± 0.25 |
|---|---|---|---|---|
| IM58 | sp\|P42655 | 14-3-3 Protein epsilon | 28.2 | 4.7 |
| IM60 | sp\|P12324 | Tropomyosin, cytoskeletal type | 28.9 | 4.6 |
| IM136 | | | 70.5 | 4.9 |
| IM403 | | | 75.1 | 4.7 |
| IM451 | | | 18.0 | 6.0 |
| IM612 | sp\|Q09666 | Neuroblast associated differentiation associated protein AHNAK fragment including at least residues: 612–1419 | 145.4 | 5.5 |
| IM791 | sp\|Q09666 | Neuroblast associated differentiation associated protein AHNAK fragment including at least residues: 612–1419 | 144.1 | 5.4 |
| IM793 | sp\|Q09666 | Neuroblast associated differentiation associated protein AHNAK fragment including at least residues: 612–1419 | 142.9 | 5.3 |
| IM794 | sp\|Q09666 | Neuroblast associated differentiation associated protein AHNAK fragment including at least residues: 612–1419 | 143.9 | 5.2 |
| IM953 | | | 44.6 | 5.9 |
| IM999 | sp\|P09211 | Glutathione transferase | 23.6 | 5.2 |
| IM1001 | | | 25.2 | 4.8 |
| NM92 | sp\|P21796 | Voltage-dependent anion channel 1 | 34.2 | 8.5 |
| NM7204 | sp\|O75334 | Liprin-alpha 2 | 130.6 | 7.9 |
| NM7283 | | | 38.2 | 9.3 |
| NM7314 | | | 27.9 | 7.8 |

TABLE 11

Endometrial proteins with decreased synthesis in secretory phase endometrium

| Spot ID | Identifier | Protein name | Observed MW ± 10% (kDa) | Observed pI ± 0.25 |
|---|---|---|---|---|
| IM260 | sp\|P30101 | Protein disulfide isomerase ER60 | 53.4 | 5.7 |
| IM439 | | | 26.3 | 6.5 |

In the above Tables 1 to 11, all accession numbers ("Identifier") beginning "sp" relate to the Swiss-Prot data-base maintained by the Department of Medical Biochemistry of the University of Geneva and the EMBL Outstation—The European Bioinformatics Institute (EBI). Those beginning "gi" relating to the National Center for Biotechnology Information—NCBI data-base.

Out of a total number of 1,390 protein spots found in the conditioned medium of endometrial tissue explants, 5 spots were found to have increased synthesis in hyperplasia. The locations of these spots are shown in FIGS. 1 and 2. From these, certain spots were selected for further use. The information obtained from the 2D gel electrophoresis with respect to isoelectric point (pI) and the molecular weight (MW) of the spots is given in Table 1. The pI and MW values were determined with reference to standards as further described below with reference to FIGS. 20 and 21. One spot was found to have decreased synthesis in hyperplasia. The location of this spot is shown in FIG. 3, and pI and MW is given in Table 2. Fourteen spots were found to have increased synthesis in adenocarcinoma. The locations of these spots are shown in FIGS. 4 and 5, and the pI and MW values of selected spots are given in Table 3. Forty-five spots were found to have decreased synthesis in adenocarcinoma. The locations of these spots are shown in FIGS. 6 and 7, and the pI and MW values of selected spots are given in Table 4. Twenty spots were found to have increased synthesis in hyperplasia and adenocarcinoma. The locations of these spots are shown in FIGS. 8 and 9, and the pI and MW values of selected spots are given in Table 5. Fifteen spots were found to have decreased synthesis in hyperplasia and adenocarcinoma. The locations of these spots are shown in FIGS. 10 and 11, and the pI and MW values of selected spots are given in Table 6. Twenty spots were found to have increased synthesis in proliferative phase endometrium. The locations of these spots are shown in FIGS. 12 and 13, and the pI and MW values of selected spots are given in Table 7. Nine spots were found to have increased synthesis in hyperplasia and proliferative phase endometrium. The locations of these spots are shown in FIGS. 14 and 15, and the pI and MW values of selected spots given in Table 8. One spot was found to have decreased synthesis in proliferative phase endometrium. The location of this spot is shown in FIG. 16, and the pI and MW value is given in Table 9. Twenty spots were found to have increased synthesis in secretory phase endometrium. The locations of these spots are shown in FIGS. 17 and 18, and the pI and MW values of selected spots are given in Table 10. Three spots were found to have decreased synthesis in secretory phase endometrium. The locations of these spots are shown in FIG. 19, and the pI and MW values of selected spots are given in Table 11.

In order to calibrate the positions of spots on the 2D gels as regards pI and MW, similar gels were run under the same conditions using a labelled extract from Hela Cells, for which the pI and MW values of several proteins have previously been determined. The spots belonging to these marker proteins can be identified in such gels by their relative positions in the pattern of spots produced. Their positions are then transferred to the endometrial protein 2D gels and the endometrial spots are allocated pI and MW values by interpolation.

The pI and MW values for the marker proteins shown in FIGS. 20 and 21 are listed in the following tables.

| List of spots for MW and pI calibration of IEF proteins | | |
|---|---|---|
| | Molecular Weight kDa | Isoelectric point |
| 1 | 116.87 | 6.01 |
| 2 | 94.75 | 4.72 |
| 3 | 81.43 | 4.84 |
| 4 | 69.94 | 4.83 |
| 5 | 98.12 | 5.20 |
| 6 | 63.13 | 5.23 |
| 7 | 66.10 | 5.01 |
| 8 | 84.33 | 5.62 |
| 9 | 69.58 | 6.12 |
| 10 | 55.25 | 5.15 |
| 11 | 98.00 | — |
| 12 | 43.65 | 5.11 |
| 13 | 44.56 | 5.01 |
| 14 | 54.69 | 4.89 |
| 15 | 57.56 | 4.89 |
| 16 | 54.97 | 4.79 |
| 17 | 95.00 | — |
| 18 | 60.28 | 4.59 |
| 19 | 36.68 | 4.47 |
| 20 | 35.20 | 4.48 |
| 21 | 30.19 | 4.50 |
| 22 | 30.97 | 4.78 |
| 23 | 35.38 | 5.56 |
| 24 | 30.97 | 5.65 |
| 25 | 30.03 | 5.48 |
| 26 | 38.21 | 5.71 |
| 27 | 35.93 | 6.42 |
| 28 | 27.67 | 6.59 |
| 29 | 28.10 | 6.35 |
| 30 | 28.83 | 6.29 |
| 31 | 25.36 | 5.79 |
| 32 | 23.61 | 5.47 |
| 33 | 25.62 | 4.51 |
| 34 | 14.51 | 4.19 |
| 35 | 15.51 | 5.57 |

| List of spots for MW and pI calibration of NEPHGE proteins | | |
|---|---|---|
| | Molecular Weight kDa | Isoelectric point |
| 1 | 95.30 | 9.19 |
| 2 | 87.76 | 7.52 |
| 3 | 58.68 | 8.18 |
| 4 | 51.06 | 7.40 |
| 5 | 44.42 | 8.14 |
| 6 | 38.65 | 7.64 |
| 7 | 42.69 | 8.64 |
| 8 | 37.52 | 8.67 |
| 9 | 36.42 | 8.67 |
| 10 | 34.31 | 8.23 |
| 11 | 29.26 | — |
| 12 | 22.60 | 8.27 |
| 13 | 17.98 | 8.23 |
| 14 | 17.11 | — |
| 15 | 17.45 | 7.75 |
| 16 | 14.89 | 8.45 |
| 17 | 13.21 | 8.56 |
| 18 | 39.43 | 9.17 |
| 19 | 35.35 | 9.67 |
| 20 | 50.55 | 9.65 |

The proteins or polypeptides described above may also be further characterised by partial amino acid sequence analysis.

It may be expected that a ratio between the amount of a protein or polypeptide having increased synthesis and the amount of a protein or polypeptide having decreased synthesis for a certain endometrial condition will be used as marker for the given endometrial condition.

The proteins or polypeptides of interest may be isolated from endo-metrial tissue or other protein sources by 2D gel electro-phoresis or by using chromatographic techniques. Poly- or monoclonal antibodies towards the protein of interest can be raised, and immunoassays can be established based on such antibodies. Synthetic peptides being fragments characteristic of such proteins may be used for the same purposes. Assays may be based on more than one such protein for measurement at one time.

Preferably, the protein or polypeptide on which an assay, antibody, cell line or kit according to this invention is based is not detectable as being produced in increased amounts by the endometrium in hyperplasia, adenocarcinoma or the proliferative phase by 2D gel electrophoresis based on tissue homogenates or cell lysates.

REFERENCES

Ref. 1: Byrjalsen et al., Hum Reprod 1995; 10:13-18.
Ref. 2: Byrjalsen et al., Mol Hum Reprod 1999; 5:748-756.
Ref. 3: Julkunen et al., Endocrinology 1986; 118:1782:1786.
Ref. 4: Byrjalsen et al. Obstet Gynecol 1992;79:523-528.
Ref. 5: Byrjalsen et al., Hum Reprod 1992;7:1042-1047.
Ref. 6: Rawal et al., Int. J. Cancer: 83,727-731 (1999).
Ref. 7: Xu et al., 1994, J. Immunol. Methods, 171, 245-52.
Ref. 8: Honda K. et al., 1998, J. Cell Biol. 140, 1383-1393.

The invention claimed is:

1. A method for detecting hyperplasia or adenocarcinoma of the endometrium in a patient, said process comprising measuring the levels of stress-induced phosphoprotein-1 in a sample of a biological fluid acquired from the patient and a sample of the biological fluid acquired from a subject having a normal endometrium, comparing the measured levels, and determining that there is an indication of the presence of hyperplasia or adenocarcinoma of the endometrium in the patient if the level of stress-induced phosphoprotein-1 in the sample of the biological fluid from the patient is higher than the level of stress-induced phosphoprotein-1 in the biological fluid of the subject having a normal endometrium, wherein said stress-induced phosphoprotein-1 comprises the amino acid sequence of SEQ ID NO: 1 (as set forth under GEN-EMBL database accession number P31948).

2. The method of claim 1, wherein said biological fluid is selected from the group consisting of blood, serum, and plasma.

* * * * *